United States Patent [19]
Leung et al.

[11] Patent Number: 6,004,536
[45] Date of Patent: Dec. 21, 1999

[54] LIPOPHILIC CYANINE DYES WITH ENCHANCED AQUEOUS SOLUBILTY

[75] Inventors: Wai-Yee Leung; Richard P. Haugland; Fei Mao, all of Eugene, Oreg.

[73] Assignee: Molecular Probes, Inc., Eugene, Oreg.

[21] Appl. No.: 08/702,396

[22] Filed: Aug. 14, 1996

Related U.S. Application Data

[60] Provisional application No. 60/006,686, Nov. 14, 1995.

[51] Int. Cl.$^6$ .......................... A61K 49/00; G01N 33/48; C07D 209/04; C07D 403/06
[52] U.S. Cl. ........................ 424/9.6; 424/10.3; 436/63; 436/172; 436/91; 436/92; 436/93; 436/96; 548/152; 548/156; 548/159; 548/217; 548/219; 548/469; 548/491; 548/494; 548/503; 548/510; 548/518
[58] Field of Search ............................. 436/63, 172, 91, 436/92, 93, 96; 548/469, 491, 494, 503, 510, 518, 152, 156, 159, 217, 219; 424/9.6, 10.3

[56] References Cited

U.S. PATENT DOCUMENTS

| | | |
|---|---|---|
| 4,762,701 | 8/1988 | Horan et al. . |
| 4,783,401 | 11/1988 | Horan et al. . |
| 4,859,584 | 8/1989 | Horan et al. . |
| 5,047,519 | 9/1991 | Hobbs, Jr. et al. . |
| 5,268,486 | 12/1993 | Waggoner et al. . |
| 5,316,906 | 5/1994 | Haugland et al. . |
| 5,321,130 | 6/1994 | Yue et al. . |
| 5,375,606 | 12/1994 | Slezak et al. ........................... 128/691 |
| 5,405,975 | 4/1995 | Kuhn et al. . |
| 5,410,030 | 4/1995 | Yue et al. . |
| 5,436,134 | 7/1995 | Haugland et al. . |
| 5,437,980 | 8/1995 | Haugland et al. . |
| 5,443,986 | 8/1995 | Haugland et al. . |
| 5,453,517 | 9/1995 | Kuhn et al. . |
| 5,459,268 | 10/1995 | Haugland et al. . |

FOREIGN PATENT DOCUMENTS

WO 93/06482 of 1993 WIPO .
93/11120 6/1993 WIPO .

OTHER PUBLICATIONS

Cohen et al., "A cyanine dye distinguishes between cycling and non–cycling fibroblasts," Nature, vol. 290, pp. 593–595, Apr. 16, 1981.
Brooker, et al., J. Am. Chem. Soc. 73, 5332 (1951).
Brooker, et al., J. Am. Chem. Soc 64, 199 (1942).
Czikkely, et al., Z. Naturforsch. 24, 1821 (1969) Abstract only.
Schlessinger, et al., Science 195, 307 (1977).
Honig, et al., J. Cell Biol. 103, 171 (1986).
Haugland, Molecular Probes Handbook of Fluorescent Probes And Research Chemicals (1992).
Hamer, et al., "Cyanine Dyes and Related Compounds," The Chemistry of Heterocyclic Compounds, vol. 18, A. Weissberger, Ed., Interscience, New York (1964).
Wittung, et al., Nature 368, 561 (1994).
Brinkley, et al., Bioconjugate Chem., 3, 2 (1992).
Makin, et al., Zh. Org. Khim. 13, 2440 (1977).

*Primary Examiner*—Johann Richter
*Assistant Examiner*—Jane C. Oswecki
*Attorney, Agent, or Firm*—Allegra J. Helfenstein; Anton E. Skaugset

[57] ABSTRACT

The present invention relates to a family of cyanine dyes possessing lipophilic alkyl chains and either one or more reactive functional groups, bromo or chloro, or phenyl, sulfophenyl or polysulfophenyl substituents or combinations thereof. The dyes of the invention are useful for staining membranes in cells or isolated from cells, and are well-retained therein. Additionally, the reactive dyes of the invention are useful for preparing dye-conjugates, thereby conferring the membrane staining ability of the subject dye onto the resulting dye-conjugate.

28 Claims, 4 Drawing Sheets

LIPOPHILIC CYANINE DYES WITH ENCHANCED AQUEOUS SOLUBILTY

This application claims the benefit of U.S. Provisional Application No. 60/006,686, filed Nov. 14, 1995.

FIELD OF THE INVENTION

The invention relates to cyanine dyes that are useful for staining lipid structures, in particular lipid structures of biological cells, tissues, liposomes and lipoproteins, and are well-retained therein, or are useful for forming conjugates of organic substances that can then be localized in lipid structures and used to track the location or identity of the labeled lipid structure.

BACKGROUND

Fluorescent dyes are known to be particularly suitable for biological applications in which a highly sensitive detection reagent is desirable. Dyes that are able to preferentially bind to a specific biological ingredient or component in a sample enable the researcher to determine the presence, quantity or location of that specific ingredient or component. In addition, specific biological systems can be monitored with respect to their spatial and temporal distribution in diverse environments.

A wide variety of symmetric and asymmetric cyanine dyes and methods for their synthesis have been described, particularly for use in the photographic industry (For example, Brooker et al., J. AM. CHEM. SOC. 73, 5332 (1951); Brooker et al., J. AM. CHEM. SOC. 64, 199 (1942)). Most cyanines possess high visible absorbance and reasonable resistance to photodegradation. Their methods of synthesis permit fine adjustments in their color by changing the aromatic components used for their synthesis or the number of methine groups between the aromatic moieties.

The general structure of cyanine dyes is given by the formula below:

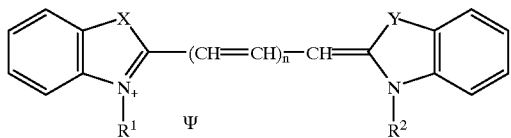

In the above formula X and Y are typically heteroatoms O, S, Se, Te, $NR^3$, or disubstituted carbon atoms $CR^3R^4$, where the substituents on the nitrogen or carbon are typically alkyl groups. Those dyes wherein n=0 are typically referred to as "cyanine" dyes. Where n=1 the dyes are termed "carbocyanine" dyes, while where n=2 the dyes are "dicarbocyanine" dyes and if n=3 the dyes are "tricarbocyanine" dyes, and so on. This class of dyes is generically referred to as "cyanine" dyes no matter the specific number of methine groups between the ring systems. Although the conjugating bridge atoms separating the aromatic rings are typically methine (—CH=) groups, bridging groups containing rings are known in the art, as are various substituents on the central carbon atom in the spacer. The substituents $R^1$ and $R^2$ are typically saturated or unsaturated alkyl groups that are optionally further substituted by a wide variety of other functional groups. The remaining substituents of the cyanine dyes have been shown to include most organic functional groups, as well as additional rings that are fused or not fused rings and that may be additionally substituted themselves.

Those cyanine dyes wherein X=Y=O and n=1 are typically known as "oxacarbocyanines", whereas those cyanine dyes wherein X=Y=S and n=1 are usually called "thiacarbocyanines" and those dyes wherein X=Y=$CR^3R^4$ and n=1 are usually called "indocarbocyanines". These classes of cyanine dyes are the most well known, along with those analogs wherein n=0, 2, or 3. For those dyes wherein $R^1$ and $R^2$ are simple alkyl chains and all other substituents are H, there exists a widely used naming system. For example, the dye known as $DiOC_{18}(3)$ (or "DiO") has X and Y are O, n=1, $R^1$ and $R^2$ are octadecyl, and (3) is the total number of methine atoms in the spacer. Similarly, for the analogous dye wherein X and Y are both $C(CH_3)_2$, n=1 and $R^1$ and $R^2$ are octadecyl, the common name is $DiIC_{18}(3)$ (or "DiI"). The analogous dyes for which X or Y is $NR^3$, Se and Te are much less common, partially due to a greater degree of synthetic difficulty in their preparation. The counterion $\Psi$ is typically an anion that balances the intrinsic positive charge of the cyanine dye; however, if the cyanine dye also contains negatively charged groups, the counterion $\Psi$ may be a cation or the molecule may be an internal zwitterion. In either case $\Psi$ is present in such a number and with such a total charge as to make the overall molecule electrically neutral.

For most carbocyanines initially described in the literature, the substituents $R^1$ and $R^2$ were methyl or ethyl, usually ethyl. However, the use of the lipophilic dyes $DiOC_{18}(3)$ and $DiIC_{18}(3)$ for staining cellular and synthetic membranes was described as early as 1969 (Czikkely, et al. Z. NATURFORSCH. 24, 1821 (1969)). Since that time the fluorescence properties of these and other structurally related dyes have been used extensively to measure the lateral mobility of the dyes in membranes (Schlessinger et al., SCIENCE 195, 307 (1977)) and more recently to trace neurons in long term cell cultures (Honig et al. J. CELL BIOL. 103, 171 (1986)). In living biological cells, the cyanine dyes in which $R^1$ and $R^2$ are both lower alkyl (usually with 6 or less carbon atoms) typically localize in intracellular organelles of live cells such as the mitochondria and the endoplasmic reticulum, where they may be toxic to the cell, whereas the dyes in which $R^1$ and $R^2$ are both greater than about 10 carbon atoms typically localize in the cellular membranes, where they are relatively nontoxic to cells. Dyes of this type have been described as being well retained by live cells and liposomes and usually not transferring to adjacent cells or to unlabeled liposomes.

The use of certain cationic lipophilic cyanine dyes, including $DiIC_{18}(3)$, $DiOC_{18}(3)$ and their $C_{12}$ to $C_{22}$ homologs in combination with an osmolarity regulating agent to stain cells for the purposes of labeling viable cells, tracking stained cells in vivo, and measuring cell growth rate has been previously described (U.S. Pat. No. 4,762,701 to Horan et al. (1988); U.S. Pat. No. 4,783,401 to Horan et al., (1988); U.S. Pat. No. 4,859,584 to Horan et al. (1989)). However, the labeling procedure used by Horan requires the use of an aqueous "osmolarity-regulating agent" that typically includes sugars, sugar-alcohols, amino acids and "Good's Buffers" in order to keep the dye in solution, as these dyes are generally very insoluble in aqueous solution. Some cell lines, however, may be sensitive to certain osmolarity-regulating agents, particularly sugar-alcohols, and it was therefore advised that users of these dyes conduct standard tests to ensure that cells are viable in the desired osmolarity-regulating agents. Additionally, the presence of inorganic salts, including the ones commonly found in standard buffers such as phosphate-buffered saline (PBS) and in normal culture medium, greatly reduces the solubility of the dyes, thereby lowering the labeling efficiency even in the presence of an osmolarity-regulating agents. Furthermore, many cells do not survive in essentially salt-free media. Finally, like other lipophilic cyanine dyes, the Horan et al. dyes can not tolerate a combined treatment of cell fixation and permeabilization with organic solvents. In histochemical studies, it is common that cells or tissues are fixed with formaldehyde or glutaraldehyde, followed by permeabilization with acetone or alcohol, which usually removes most of the lipids associated with the cell membranes, so that the inside of the cells becomes accessible to macromolecules such as antibodies or labeled antibodies.

Waggoner et al. describes reactive cyanine dyes useful for forming covalent bonds with proteins and other materials (U.S. Pat. No. 5,268,486 to Waggoner et al., (1993)). These particular cyanine dyes are required to contain reactive groups and are required to be sulfonated. However, the Waggoner et al. dyes do not contain lipophilic residues at $R^1$ and $R^2$, and are not useful for labeling or studying membranes.

SUMMARY OF THE INVENTION

The present invention relates to a family of cyanine dyes possessing lipophilic alkyl chains and either a reactive functional group, or a phenyl, sulfo, sulfophenyl, or a bromo or chloro substituent. The dyes of the invention are useful for staining lipophilic structures, such as membranes in cells or tissues, membranes isolated from cells, natural or artificial liposomes, lipoproteins or polymers. Additionally, the sulfonated dyes of the invention are typically anionic or polyanionic and are more readily dissolved into aqueous staining media, including typical media used for cell cultures, than the cationic lipophilic dyes described by Horan (supra). Once a sample has been stained, the dyes of the invention are well-retained within the sample. The sulfonated- and chemically reactive- dyes of the invention typically resist extraction with the organic solvents typically used in histochemistry for cell permeabilization before the use of secondary detection reagents.

Additionally, the reactive dyes of the invention are useful for preparing dye-conjugates of organic substances, including conjugates of specific binding pairs, thereby conferring the membrane staining ability of the subject dye onto the resulting dye-conjugate, and allowing anchoring of an organic substance of interest to a membrane, where the fluorescence of the cyanine dye allows precise monitoring of the location of the dye-conjugate.

DESCRIPTION OF THE PREFERRED EMBODIMENTS

Figure 1:
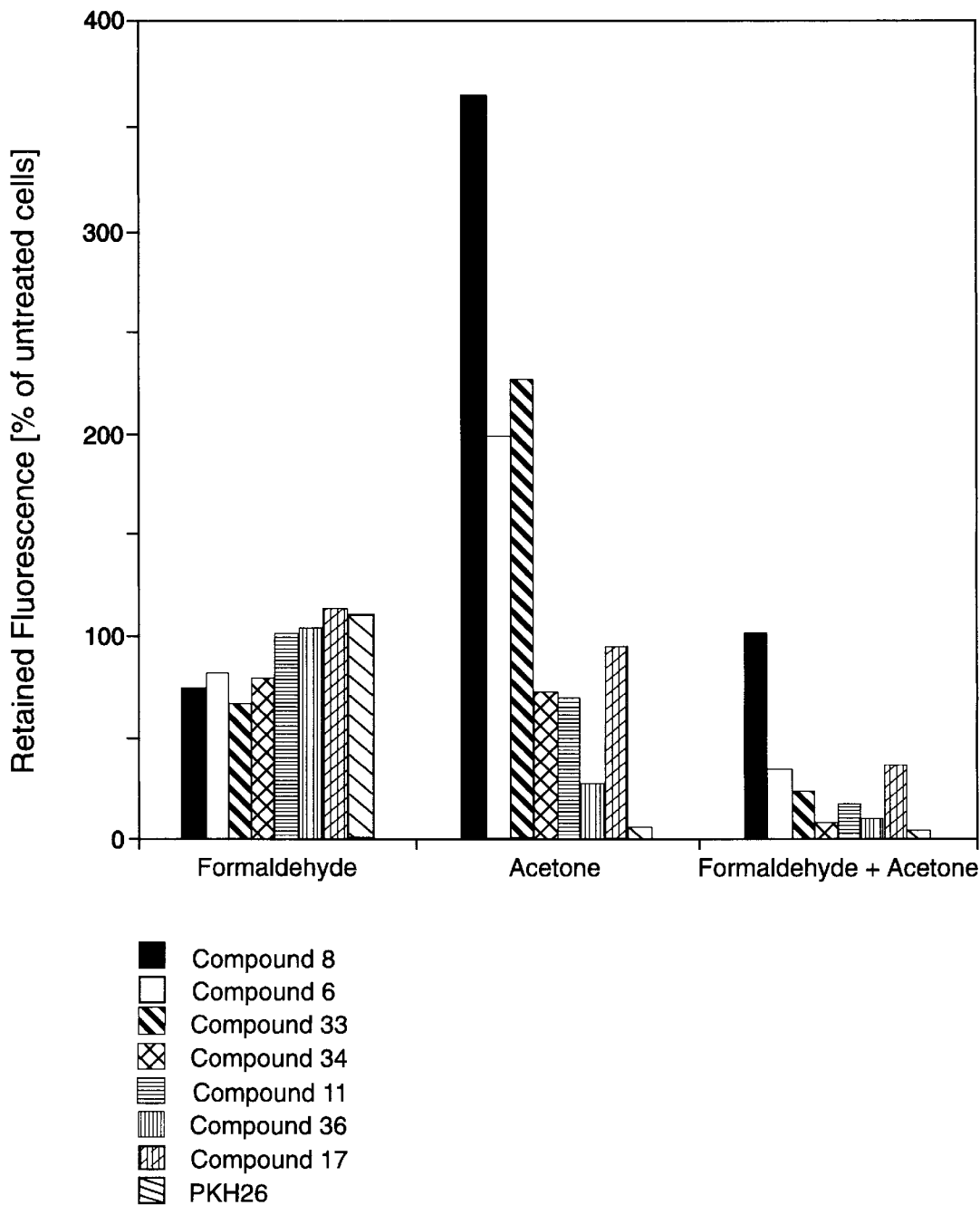
FIG. 1: A graphic depiction showing the relative fluorescence intensities of cells stained with Compounds 8, 6, 33, 34, 11, 36, 17 and the commercially available cyanine dye PKH26 (Sigma Chemical Co., St. Louis, Mo.) after treatment of the cells with 1) formaldehyde, 2) acetone or 3) formaldehyde followed by acetone.

The dyes of the invention have the general formula

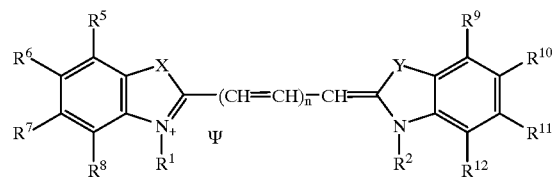

wherein $R^1$ and $R^2$ are independently linear or branched hydrocarbons having 7–30 carbons. Each hydrocarbon is optionally completely saturated, or contains unsaturated elements, including incorporation of a 5- or 6-membered unsaturated hydrocarbon ring. In addition, each hydrocarbon is independently and optionally substituted one or more times by fluoro or chloro atoms or by an alkoxy group having 1–6 carbons. Typically $R^1$ and $R^2$ or both are linear saturated or unsaturated hydrocarbons. In another embodiment, $R^1$ or $R^2$ or both optionally incorporate 1 or 2 phenylene groups, preferably 1 phenylene group per alkyl substituent. Where $R^1$ and $R^2$ are linear saturated hydrocarbon chains, they typically have 7–26 carbons, preferably 12–22 carbons, more preferably 14, 16, 18, 20 or 22 carbons. Preferably $R^1=R^2$.

The benzazole ring fragments X and Y are independently O, S or $CR^3R^4$, where $R^3$ and $R^4$, which may be the same or different, are independently alkyl groups having 1–6 carbons. Alternatively, $R^3$ and $R^4$ taken in combination complete a 5- or 6-membered saturated ring. Preferably X=Y (yielding a symmetrical cyanine). More preferably both X and Y are $CR^3R^4$ or O. Typically $R^3$ and $R^4$ are methyl or ethyl, more typically methyl.

The two benzazole rings are linked by a methine bridge, —(CH=CH)$_n$—CH=. When n=0 the dyes are monomethine dyes; when n=1 the dyes are trimethine dyes; when n=2, the dyes are pentamethine dyes, etc. As with similar compounds, the number of methine groups between the heteroaromatic rings influences the spectral properties of the dye. The monomethine dyes of the present invention typically have blue to green fluorescence emission. The trimethine dye analogs are substantially shifted toward red wavelengths, and the pentamethine dyes are shifted even further, often exhibiting infrared fluorescence emission. Preferably n=1 or 2.

The methine bridge itself is typically unsubstituted, or is optionally substituted by F, Cl, or alkyl having 1–6 carbons. Alternatively, any double bond in the methine bridge is optionally incorporated into a 5- or 6-membered hydrocarbon ring that is unsubstituted or is optionally substituted one or more times by alkyl having 1–6 carbons. Preferably the 5- or 6-membered ring occurs at the center of a heptamethine bridge, as shown below:

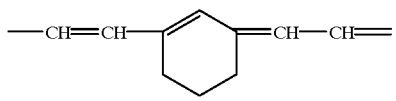

The benzazole substituents $R^5$, $R^6$, $R^7$, $R^8$, $R^9$, $R^{10}$, $R^{11}$ and $R^{12}$ are independently hydrogen, halogen, CN, sulfo, carboxy, amino, ammonium, phenyl, sulfophenyl, polysulfophenyl, methylbenzamido (—NH—(C=O)—$C_6H_4$—$CH_3$), or an alkyl group having 1–22 carbons that is optionally and independently substituted by one or more or F, Cl or —$OR^{13}$ where $R^{13}$ is H or an alkyl group having 1–6 carbons. Alternatively, any two adjacent substituents of $R^5$, $R^6$, $R^7$, $R^8$, $R^9$, $R^{10}$, $R^{11}$ and $R^{12}$, when taken in combination, form a fused benzo substituent. Benzo-substituted cyanines, e.g. naphthocyanines, typically have longer wavelength spectral properties than the corresponding derivatives that do not have the benzo substituent. In yet another alternative, any of $R^5$, $R^6$, $R^7$, $R^8$, $R^9$, $R^{10}$, $R^{11}$ and $R^{12}$ is optionally a reactive group —L—A.

Preferably, the dyes of the invention are symmetric, such that $R^5$=$R^9$, $R^6$=$R^{10}$, etc. Also preferably the dye contains one or two benzazole substituents that are water solubilizing groups, such as sulfo, carboxy or their salts.

For all dyes of the invention, any net positive or negative charges possessed by the dye are balanced by a biologically compatible counterion or counterions. As used herein, a substance that is biologically compatible is not toxic as used, and does not have a substantially deleterious effect on biomolecules. Where necessary, the counterion is depicted as Ψ and the polarity of the charge is indicated. Any of the common counterions currently used in conjunction with biomolecules is a suitable counterion for the dyes of the present invention. Examples of useful counterions for dyes having a net positive charge include, but are not limited to, chloride, bromide, iodide, sulfate, alkanesulfonate, arylsulfonate, phosphate, perchlorate, tetrafluoroborate, nitrate and anions of aromatic or aliphatic carboxylic acids. Preferred negative counterions are chloride, iodide, perchlorate and various sulfonates. Examples of useful counterions for dyes having a net negative charge include, but are not limited to, alkali metal ions, alkaline earth metal ions, transition metal ions, ammonium or substituted ammonium ions.

In one embodiment of the invention, at least one of $R^5$, $R^6$, $R^7$, $R^8$, $R^9$, $R^{10}$, $R^{11}$ or $R^{12}$ is the link-reactive group moiety —L—A. For all embodiments, no more than one of $R^5$, $R^6$, $R^7$ and $R^8$ is an —L—A, and no more than one of $R^9$, $R^{10}$, $R^{11}$ and $R^{12}$ is an —L—A. In this embodiment the dyes of the invention are reactive cyanine dyes suitable for forming conjugates of organic materials. Preferably at least one of $R^6$, $R^7$, $R^{10}$ and $R^{11}$ are an —L—A.

In another embodiment of the invention, at least one of $R^5$, $R^6$, $R^7$, $R^8$, $R^9$, $R^{10}$, $R^{11}$ or $R^{12}$ is a phenyl, sulfo, sulfophenyl or polysulfophenyl substituent. Preferably, no more than one of $R^5$, $R^6$, $R^7$ and $R^8$ is a phenyl, sulfo, sulfophenyl or polysulfophenyl and no more than one of $R^9$, $R^{10}$, $R^{11}$ and $R^{12}$ is a phenyl, sulfo, sulfophenyl or sulfophenyl. More preferably, the phenyl, sulfo, sulfophenyl or polysulfophenyl substituents are substituted symmetrically on the cyanine dye. In this embodiment the dyes of the invention possess enhanced photostability, water solubility and quantum yield.

In yet another embodiment of the invention, at least one of $R^5$, $R^6$, $R^7$, $R^8$, $R^9$, $R^{10}$, $R^{11}$ or $R^{12}$ is a bromo or chloro substituent. Generally, no more than two of $R^5$, $R^6$, $R^7$ and $R^8$ is a bromo or chloro, and no more than two of $R^9$, $R^{10}$, $R^{11}$ and $R^{12}$ is a bromo or chloro; preferably, no more than one of $R^5$, $R^6$, $R^7$ and $R^8$ is a bromo or chloro, substituent and no more than one of $R^9$, $R^{10}$, $R^{11}$ and $R^{12}$ is a bromo or chloro substituent. More preferably, the bromo or chloro substituents are substituted symmetrically on the cyanine dye. Preferred embodiments of these dyes possess enhanced quantum yield.

The linking moiety, L, is a single covalent bond, or L is a covalent linkage having 1–20 nonhydrogen atoms selected from the group consisting of C, N, O and S, such that the linkage contains any combination of bonds selected from the group consisting of ether, thioether, amine, ester, carboxamide, sulfonamide or hydrazide bonds; single, double, triple or aromatic carbon-carbon bonds; or aromatic or heteroaromatic bonds. Typically L moieties are composed of any combination of single carbon-carbon bonds and carboxamide bonds, optionally containing a phenylene moiety. Selected examples of L moieties optionally include methylenes, oligomethylenes, phenylenes, carboxamides, and sulfonamides. In one embodiment of the invention, LINK has the formula —$(CH_2)_a(CONH(CH_2)_b)_z$—, where a has any value from 0–5, b has any value from 1–5 and z is 0 or 1. Typically, L is a single bond or a polymethylene having 1–6 carbons, or L is a single covalent bond, a carbonyl, or phenylene.

The reactive group, A, is a functional group that is chemically reactive (or that can be made chemically reactive) with the functional groups typically found in biological materials or polymers, or functional groups that can be readily converted to chemically reactive derivatives using methods well known in the art (Haugland, MOLECULAR PROBES HANDBOOK OF FLUORESCENT PROBES AND RESEARCH CHEMICALS, Sets 1–11, (1992)).

In one embodiment of the invention, the reactive group A is a halomethyl (—$CH_2$—X), haloacetamide (—NH—(C=O)—$CH_2$—X) or a halomethylbenzamide (—NH—(C=O)—$C_6H_4$—$CH_2$—X), where X is Cl, Br or I. Alternatively, A is an amine, a maleimide

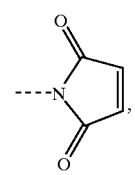

an azido, a (3,5-dichloro-2,4,6-triazin-1-yl)amino

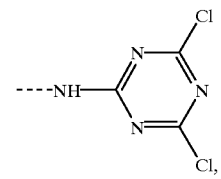

an isocyanato (—N=C=O), an isothiocyanato (—N=C=S), an acyl halide, a succinimidyl ester, or a sulfosuccinimidyl ester.

Selected embodiments of —L—A include a maleimidyl benzamide

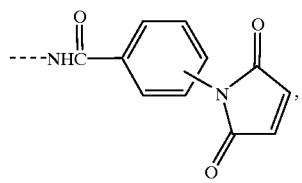

a maleimidyl alkylamido

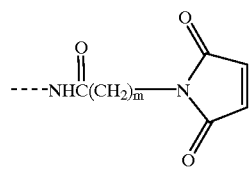

(where m=1 to 5),
an azidobenzamido

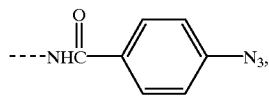

or an azidoperfluorobenzamido

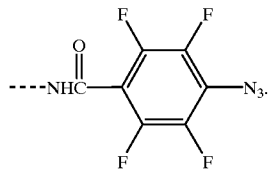

In another embodiment of the invention, the reactive group A is a carboxylic acid (—COOH), or a derivative of a carboxylic acid. An appropriate derivative of a carboxylic acid includes an alkali or alkaline earth metal salt of a carboxylic acid. Alternatively, A is a reactive derivative of a carboxylic acid (—COOR$_x$), where the reactive group R$_x$ is one that activates the carbonyl group of —COOR$_x$ toward nucleophilic displacement. In particular, R$_x$ is any group that activates the carbonyl towards nucleophilic displacement without being incorporated into the final displacement product.

Typically, R$_x$ is selected so as to make A an activated ester of a carboxylic acid: for example R$_x$ is selected to as to make A a simple mixed anhydride of the cyanine dye and a $C_2$–$C_8$ chloroformate, a $C_2$–$C_8$ carboxylic acid or perfluorinated carboxylic acid, a $C_1$–$C_8$ sulfonic or fluorinated sulfonic acid. Alternatively, A is an acyl azide. A is alternatively a carboxylic acid activated by a carbodiimide. Finally, A is an ester of a phenol or a naphthol that is further substituted by at least one strong electron withdrawing group. Selected electron withdrawing groups, present in any combination, include but are not limited to nitro, sulfo, carboxy, alkali or alkaline earth metal salt of sulfo or carboxy, cyano, fluoro or chloro, or trifluoromethyl. Particularly suitable substituted aryl esters include nitrophenyl, pentafluorophenyl and pentachlorophenyl esters.

Additional A groups include, among others, acyl nitriles, carbodiimide-activated carboxylic acids, acyl hydrazides, sulfonyl halides, sulfonyl azides, alcohols, thiols, semicarbazides, hydrazines, or hydroxylamines.

Preferably the reactive group A is a halomethyl, particularly chloromethyl, or A is an amine or a succinimidyl ester, all of which are either directly linked to the dye or are linked through linking groups L, as defined previously.

TABLE 1

Selected Cyanine Dyes*

| Compound | Dye Structure |
|---|---|
| DiI | 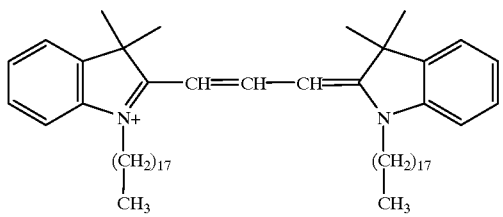 |
| DiO | 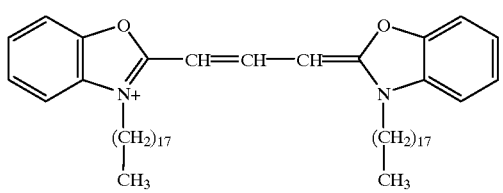 |

TABLE 1-continued

Selected Cyanine Dyes*

| Compound | Dye Structure |
|---|---|
| 5 | |
| 6 | |
| 8 | |
| 11 | |
| 12 | |
| 17 | |

TABLE 1-continued

Selected Cyanine Dyes*

Compound  Dye Structure 32, 33, 34, 35, 36, 37 — cyanine dye structures

TABLE 1-continued

Selected Cyanine Dyes*

| Compound | Dye Structure |
|---|---|
| 38 | 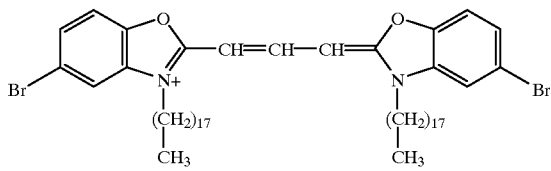 |

*It is understood that, where necessary, the dyes depicted herein include a biologically compatible counterion, Ψ, having a charge appropriate to balance the charges present on the dye.

TABLE 2

Spectral Data for Selected Indocarbocyanine Dyes[†]

| Compound | Extinction Coefficient ($\times 10^3$) | Absorbance Maximum | Emission Maximum | Quantum Yield[‡] |
|---|---|---|---|---|
| DiI | 140 | 550 | 565 | 1.0 |
| 5 | 160 | 556 | 573 | 1.6 |
| 6 | 164 | 557 | 573 | 1.9 |
| 11 | 144 | 555 | 570 | 1.8 |
| 12 | 214 | 650 | 679 | — |
| 17 | 136 | 553 | 570 | 1.3 |
| 32 | 140 | 576 | 599 | 2.2 |
| 33 | 160 | 577 | 600 | 1.8 |
| 34 | 140 | 552 | 568 | — |
| 35 | 140 | 557 | 572 | 1.5 |
| 36 | 133 | 553 | 570 | 1.3 |

[†]All spectral data are recorded in methanol solution.
[‡]Quantum yields in Table 2 are given relative to that of DiI = 1.0.

TABLE 3

Spectral Data for Selected Oxacarbocyanine Dyes[†]

| Compound | Extinction Coefficient ($\times 10^3$) | Absorbance Maximum | Emission Maximum | Quantum Yield[‡] |
|---|---|---|---|---|
| DiO | 154 | 484 | 501 | 1.0 |
| 8 | 169 | 496 | 513 | 2.2 |
| 37 | 175 | 497 | 513 | 2.4 |
| 38 | 155 | 489 | 506 | 1.7 |

[†]All spectral data are recorded in methanol solution.
[‡]Quantum yields in Table 3 are given relative to that of DiO = 1.0.

Synthesis

Cyanine dyes have been widely used in the photographic and textile industries, and their synthesis is well documented (Hamer et al., "Cyanine Dyes and Related Compounds," The Chemistry of Heterocyclic Compounds, vol. 18, A. Weissberger, Ed., Interscience, New York (1964)). The procedures described herein offer a general approach to the synthesis of the dyes in this invention. In brief, synthesis of the dyes is accomplished by combining the constituent parts of the dyes: the two benzazolium moieties and the methine or polymethine bridge, each of which is either commercially available or is readily prepared synthetically.

The benzazolium moiety

A wide variety of benzazolium intermediates for use in preparing photographic dyes have been described, in particular by Brooker and his colleagues (Brooker, et al., J. AM. CHEM. SOC., 64, 199 (1942)). These synthetic precursors have the structures as follows (the two precursors below are identical, but are depicted as the "left" or "right" half of the dyes of the invention for ease of visualization):

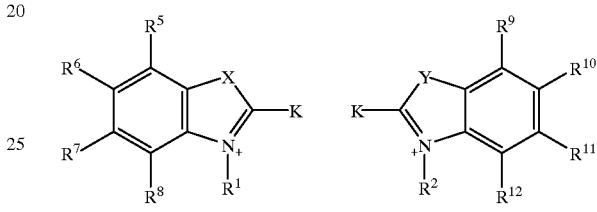

If X or Y is O, the precursor compound is a benzoxazolium; if X or Y is S it is a benzothiazolium; if X or Y is Se it is a benzoselenazolium; if X or Y is Te, it is a benzotellurazolium; and if X or Y is $CR^3R^4$ (as defined previously) then it is an indolinium derivative. Commonly $R^3$ and $R^4$ are both methyl. However, methods for preparing compounds where $R^3$ and $R^4$ are not methyl are known. Benzo substituted benzazolium precursors (naphthazole compounds) are commercially available or are readily prepared by published procedures.

The $R^1$ and $R^2$ groups are optionally incorporated in the benzazole precursor prior to ring cyclization; however, $R^1$ and $R^2$ are typically obtained by alkylation of the parent heterocycle with an alkylating agent R—Z, where Z typically becomes a charge-balancing counterion, Ψ.

K is a substituent whose nature is determined by the synthetic method used to couple the two benzazolium precursors, which may be the same or different. Depending on the compound desired and the synthetic method used, K is either methyl, or K is a leaving group. When n=0, the K group on one of the aromatic precursors is typically methyl, and the leaving group on the other is typically alkylthio (commonly methylthio) or chloro, bromo or iodo. In the synthetic precursors shown above, one precursor contains a methyl group and the other contains K, but either precursor could contain K. If the methine bridge is unsubstituted at the positions adjacent to the benzazolium rings and n=1, 2 or 3, then K is methyl on both precursors. Only when K is methyl or methylene is any part of K incorporated in the final compound.

Synthesis of the cyanine dyes

The unsymmetrical cyanine dyes wherein n is greater or equal to 1 are normally synthesized by first reacting a coupling agent with one of the benzazolium moieties to form a reactive intermediate that is then coupled to the second benzazolium moiety in the presence of a base, usually N,N-diisopropylethylamine in combination with acetic anhydride. The polymethine bridging moiety, which has the general formula —$(CH=CH)_n$—CH=, usually originates from the coupling agent used in the dye construction: e.g. N,N'-diphenylformamidine yields n=1; malonaldehyde bis (phenylimine) hydrochloride yields n=2; and glutaconaldehyde dianil monochloride yields n=3.

Cyanine dyes having a monomethine bridge are typically synthesized by treating a derivative of 2-alkylthiobenzazolium with one equivalent of a 2-methylbenzazolium derivative in the presence of a base.

While the above methods are suitable for preparing both symmetrical cyanine dyes and unsymmetrical cyanine dyes, symmetrical cyanine dyes with n greater than or equal to 1 are more commonly prepared by heating a pyridine solution containing an appropriate amount of the desired benzazolium precursor and a coupling agent. Preferred coupling agents are triethylorthoformate (for n=1); 1,1,3,3-tetramethoxypropane (for n=2) and glutaconaldehyde dianil monohydrochloride (for n=3).

If necessary, the counterion $\Psi$ is exchanged by means well known in the art, including but not limited to ion exchange chromatography, precipitation in the presence of a large excess of a salt of $\Psi$ or selective extraction or precipitation of the salt with an organic solvent.

Benzazole substituents

The aromatic substituents on the dyes of the invention are optionally introduced at different stages of the preparation of the dye, depending on the nature of the substituent.

Alkyl, haloalkyl, alkoxy, carboxyl, phenyl and halogen substituents at aromatic carbons are typically already present as substituents on the commercially available benzazole precursors, or on compounds that are readily converted to benzazole precursors using methods well-known in the art. Sulfonic acid groups are typically introduced on the precursors prior to condensation of the cyanine dye. Aminoalkyl groups are typically substituted by a protecting group when they are first introduced, typically by substitution onto the benzazole precursor. The protecting group is then removed after condensation of the cyanine dye. Aromatic amino groups are prepared via the reduction of a nitro substituted benzazolium precursor, which in turn is prepared by the nitration of the benzazole precursor.

Common reactive groups

Numerous examples of chemically reactive functional groups are known, several of which are routinely used to react with the functional groups common in biomolecules (typically amines, thiols, carboxylic acids, alcohols, phenols, aldehydes and ketones). Other functional groups, such as aryl azides, react indiscriminantly with nearby residues following ultraviolet photolysis. Dyes having common reactive groups (A) that are amino, hydroxy- or thiol-reactive or are photoaffinity labels are typically prepared from preformed dyes containing appropriate precursor substituents, using methods well-known in the art. For example:

1) Succinimidyl esters are typically prepared from dyes having a carboxylic acid substituent using N-hydroxysuccinimide and dicyclohexylcarbodiimide.

2) Acid chlorides are typically prepared from dyes containing carboxylic acid substituents using oxalyl chlorides or thionyl chloride.

3) Isocyanates are typically prepared from dyes containing amine groups using phosgene.

4) Isothiocyanates are typically prepared from dyes having amino substituents using thiophosgene.

5) Reactive haloalkyl groups are typically prepared from dyes having amino groups and an amino-reactive haloacyl or halomethylbenzoyl compound.

6) Photoaffinity labels are typically incorporated by reaction of an amine-containing dye and a known photoaffinity label that also contains an amine-reactive group.

7) Maleimido groups are typically prepared from an amine-containing dye and maleic anhydride.

Alternate synthetic routes to the above reactive functional groups utilize other reagents that are known in the art, and the above methods of preparation are not intended to limit the preparation of the dyes of the current invention to these methods or these reactive groups.

Dye-Conjugates

The dyes of the invention that possess an —L—A moiety are capable of reacting with functional groups on other materials, or are capable of being converted into reactive dyes that are capable of reacting with functional groups on other materials. Some examples of this type of reactivity include:

1. The activation of amine groups to yield reactive species, including isocyanates, isothiocyanates, 4,6-dichloro-1,3,5-triazines, maleimides, haloacetamides, halomethylbenzamides and azides;

2. The conversion of carboxylic acid groups to activated derivatives, including symmetric and mixed anhydrides, acid halides, acyl azides, acyl hydrazides and various activated esters, including succinimidyl esters, p-nitrophenyl esters and pentafluorophenyl esters;

3. The conversion of alcohol groups to ethers, esters, urethanes, carbonates or alkylating agents that include sulfonate esters and halides;

4. The conversion of thiols to thioethers, thioesters and disulfides.

The reactive dyes of the invention are used to label organic substances to form dye-conjugates by the intermolecular reaction of the reactive group A with an appropriate functional group on the organic substance to be conjugated. Appropriate organic substances for conjugation can either be isolated from natural products, prepared synthetically, or isolated from a natural product and then synthetically modified (semi-synthetic). The reactive dyes can label a wide variety of organic substances, provided that the organic substance contains a functional group that possesses suitable reactivity with any one of the reactive groups, A, that are described above. Useable functional groups on the organic substance include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, or carboxylic acids. Amines, thiols, carboxylic acids and alcohols are the preferred functional groups for conjugation, as they are both more reactive and more commonly available for the modification of biomolecules. However, a wide variety of other functional groups react under conditions well understood by one skilled in the art (as listed in Table 4). The latter include hydrazine derivatives, hydroxylamine derivatives, thioethers, and di- and trisubstituted amines. The functional group on the organic substance may be attached directly, or attached via any useful spacer or linker. A dye-conjugate is prepared from either a readily-available organic substance, or from an initially non-reactive organic substance that has been derivatized by an appropriate functional group (as above).

TABLE 4

Examples of some routes to useful conjugations

| REACTIVE GROUP A (on cyanine dye) | FUNCTIONAL GROUP (attached to organic substance) | TO YIELD: (covalent linkage) |
|---|---|---|
| alcohols/phenols | alkyl halides | ethers |
| alcohols/phenols | carboxylic acids | esters |
| alcohols/phenols | isocyanates | urethanes |
| alcohols/phenols | silyl halides | silicates |
| haloacetamides | thiols | thioethers |
| maleimides | thiols | thioethers |
| alkyl halides | thiols | thioethers |
| alkyl sulfonates | thiols | thioethers |
| alkyl halides | alcohols/phenols | ethers |
| alkyl sulfonates | alcohols/phenols | ethers |
| isocyanates | alcohols/phenols | urethanes |
| thiols | sulfonate esters | thioethers |
| thiols | haloacetamides | thioethers |
| thiols | maleimides | thioethers |
| thiols | epoxides | thioethers |
| amines/anilines | sulfonyl halides | sulfonamides |
| amines/anilines | carboxylic acids | carboxamides |
| amines/anilines | anhydrides | carboxamides |
| amines/anilines | activated esters* | carboxamides |
| amines/anilines | alkyl halides | alkyl amines |
| amines/anilines | isocyanates | ureas |
| amines/anilines | isothiocyanates | thioureas |
| amines/anilines | chlorotriazines | aminotriazines |
| amines/anilines | sulfonate esters | alkyl amines |
| carboxylic acids | amines/anilines | carboxamides |
| anhydrides | amines/anilines | carboxamides |
| acyl halides | amines/anilines | carboxamides |
| aryl azides | amines/anilines | carboxamides |
| activated esters* | amines/anilines | carboxamides |
| chlorotriazines | amines/anilines | aminotriazines |
| sulfonyl halides | amines/anilines | sulfonamides |
| isocyanates | amines/anilines | ureas |
| isothiocyanates | amines/anilines | thioureas |
| acrylamides | alkylenes | polyalkylenes |

*as described previously

Dyes that are selected to conjugate with substances or materials having free amine groups are preferably those dyes of the invention for which A is a succinimidyl ester or sulfosuccinimidyl ester. Amine-reactive dyes are of particular relevance as they are commonly used to label proteins and polypeptides, which possess free amine groups. Amine-reactive dyes are additionally used to label materials that have been substituted with free amine groups, such as amino-dextrans, or amine-containing nucleotides, oligonucleotides or nucleic acids.

Dyes that are selected to conjugate with materials having free thiol groups are preferably those dyes of the invention for which A is a haloacetamidyl, halomethylbenzamidyl, or a maleimidyl group. More preferably, A is an iodoacetamidyl or halomethylbenzamidyl. A is optionally directly linked to the dye or indirectly linked via the linker L.

Preferred alcohol- and phenol-reactive dyes are those dyes of the invention for which A is an isocyanato or (3,5-dichloro-2,4,6-triazinyl)amino.

Preferred photoreactive dyes are dyes wherein A is an azidoperfluorobenzamido group.

In one embodiment of the invention, the conjugated substance is an amino acid, peptide, or protein. By amino acid is meant any of the natural amino acids, as well as synthetic variations commonly known and utilized in the art. Common synthetic variations include amino acids that are protected on their amino, carboxylic acid, hydroxy or other functional group. Both peptides and proteins fall under the general category of peptides. While the specific demarcation line between peptides and proteins is not exact, it is typically recognized in the art that peptides have molecular weights of less than about 5,000 to 10,000 daltons, and proteins have molecular weights greater than about 5,000 to 10,000 daltons. Proteins typically possess at least secondary structure, and most often tertiary and quaternary structure. The conjugated protein is optionally present within a membrane, such as a cell membrane.

The protein conjugates of the present invention encompass a variety of proteins, including but not limited to enzymes, antibodies, lectins, glycoproteins, lipoproteins, avidin, streptavidin, protein A, protein G and phycobiliproteins. By enzyme is meant any of a group of catalytic proteins that are produced by living cells and that mediate and promote the chemical processes of life without themselves being altered or destroyed. Examples of appropriate enzymes suitable for conjugation include, but are not limited to, peroxidases, proteases, phosphatases, and glycosidases, such as β-D-galactosidases, and β-D-glucuronidases. Antibodies, as used herein, are any of various proteins synthesized by animals in response to the presence of a foreign substance, for example, immunoglobulin G (IgG) and its fragments. Lectins, as used herein, are any of various proteins that selectively bind carbohydrates, such as cell surface carbohydrates, which can be used to identify cell type. Appropriate lectins are typically isolated from plants, preferably legumes, or from bacteria, fish or invertebrates. A preferred lectin is wheat germ agglutinin. Glycoproteins, as used herein, are any of a class of conjugated proteins containing both carbohydrate and protein units. Phycobiliproteins are any of several proteins isolated from algae, including but not limited to B-phycoerythrin, R-phycoerythrin, C-phycocyanine or allophycocyanin.

In another embodiment of the invention, the conjugated substance is a single base, single nucleoside, single nucleotide or a nucleic acid polymer. By nucleotide is meant the basic structural unit of a nucleic acid, comprising an ester of a nucleoside and one or more phosphoric acid or polyphosphoric acid groups, optionally containing an additional linker or spacer for attachment of a fluorophore or other ligand, such as an alkynyl linkage (U.S. Pat. No. 5,047,519 to Hobbs, Jr. et al., (1991), incorporated by reference) or other linkage.

Nucleic acid polymers are typically large, chainlike molecules containing phosphoric acids, sugars, and purine and pyrimidine bases. Polymers that are oligonucleotides are typically composed of fewer than 50 nucleotides, more typically composed of fewer than 25 nucleotides. Oligonucleotides are optionally deoxyribonucleic acid polymers (DNA) or ribonucleic acid polymers (RNA), or a hybrid thereof. Suitable oligonucleotides are optionally antisense oligonucleotides, or strands of DNA having a sequence identical to messenger RNA. DNA polymers are optionally single-stranded (ss), double-stranded (ds), triple-stranded or quadruple-stranded DNA. RNA is optionally single-stranded or double-stranded nucleic acid polymers. The nucleic acid polymer may be a natural polymer (biological in origin) or a synthetic polymer (modified or prepared artificially). The nucleic acid polymer optionally incorporates an unusual linker such as morpholine derivatized phosphates (AntiVirals, Inc., Corvallis Oreg.), or peptide nucleic acids such as N-(2-aminoethyl)glycine units (Wittung, et al., NATURE 368, 561 (1994)). In one embodiment of the invention, the dye is attached to the nucleotide, oligonucleotide or nucleic acid polymer via one or more purine or pyrimidine bases through an amide, ester, ether or thioether bond. In another embodiment of the invention, the dye is attached to the phosphate or carbohydrate by a bond that is an ester, thioester, amide, ether or thioether. In one embodiment of the invention, where the conjugated substance is a nucleotide, the reactive group A on the reactive dye is a carboxylic acid, a derivative of a carboxylic acid, or an activated ester of a carboxylic acid. Preferably, the reactive group A is a succinimidyl ester or a sulfosuccinimidyl ester.

In another embodiment of the invention, the conjugated substance is a carbohydrate. By carbohydrate is meant any of the group of organic compounds composed of carbon, hydrogen and oxygen, including sugars, starches and celluloses. In particular, carbohydrates includes polysaccharides such as dextran, FICOL, heparin, glycogen, amylopectin, mannan, inulin, starch, agarose and cellulose. All of these polysaccharides are readily available at low cost, high purity, low background absorbance and fluorescence and have relatively uniform physical properties. Preferably a carbohydrate conjugate is a dextran or FICOL conjugate, more preferably a dextran conjugate.

In another embodiment of the invention, the conjugated substance is a lipid. By lipid is meant one of a class of compounds that contains long-chain aliphatic hydrocarbons and their derivatives, such as fatty acids, alcohols, amines, amino-alcohols, and aldehydes. The class of lipids include glycolipids, phospholipids and sphingolipids. Glycolipids are lipids that contain carbohydrate units. Phospholipids are lipids containing esters of phosphoric acid containing one or two molecules of fatty acid, an alcohol, and generally a nitrogenous base. Sphingolipids are lipids, such as sphingomyelin, that yield sphingosine or one of its derivatives as a product of hydrolysis. Alternatively, the conjugated substance is a lipid vesicle or a cell membrane.

Alternatively, the conjugated substance is a phosphoglycerol, resulting in a dye-conjugate that may be used as a phospholipid that becomes fluorescent when localized in cell membranes. In another alternative, the conjugated substance is a platelet activating factor (or PAF).

One class of conjugates of the present invention includes conjugates of biologically active molecules. Biologically active molecules include, but are not limited to, cytokines such as lymphokines, hormones, steroids, toxins, or drugs. Alternatively, conjugates of the present invention are conjugates of members of a specific binding pair, such as an antigen or a hapten. In another embodiment, the instant conjugates are conjugates of metabolites, or environmental pollutants.

Alternatively, the conjugates of the present invention are conjugates of cellular systems, cellular fragments, or subcellular particles. Examples of this type of conjugated material include virus particles, bacterial particles, virus components, biological cells, or cellular components. Examples of cellular components that can be labeled, or whose constituent molecules can be labeled, include lysosomes, endosomes, cytoplasm, nuclei, mitochondria, Golgi apparatus and vacuoles.

Finally, the conjugates of the present invention are optionally dye-conjugates of polymers, polymeric particles, polymeric membranes, conducting and non-conducting metals and non-metals, and glass and plastic surfaces and particles.

Conjugates of most low molecular weight drugs, peptides, toxins, nucleotides, phospholipids and other organic molecules are prepared by organic synthesis methods using the reactive dyes of the invention, by means well recognized in the art (Haugland, MOLECULAR PROBES HANDBOOK, Sets 1–7, (1992)). Preferably, conjugation to form a covalent bond consists of simply mixing the reactive dyes of the present invention in a suitable solvent in which both the reactive dye and the substance to be conjugated are soluble. The reaction preferably proceeds spontaneously without added reagents at room temperature or below. For those reactive dyes that are photoactivated, conjugation requires illumination of the reaction mixture to activate the reactive dye.

Conjugates of polymers, including biopolymers and other higher molecular weight polymers are typically prepared by means well recognized in the art (for example, Brinkley et al., BIOCONJUGATE CHEM., 3, 2 (1992)). In these cases, a single type of reactive site may be available, as is typical for polysaccharides) or multiple types of reactive sites (e.g. amines, thiols, alcohols, phenols) may be available, as is typical for proteins and cell membranes. Selectivity of labeling is best obtained by choice on an appropriate reactive dye. For example, modification of thiols with a thiol-selective reagent such as a haloacetamide or maleimide, or modification of amines with an amine-reactive reagent such as an activated ester, acyl azide, isothiocyanate or 3,5-dichloro-2,4,6-triazine. Partial selectivity can also be obtained by careful control of the reaction conditions.

Where dye-conjugates are prepared using a photoreactive dye of the invention, such as an azidobenzamide derivative, the conjugation requires illumination of the dye by light having a suitable wavelength, typically <400 nm.

Use of Dye-Conjugates

The dye-conjugates of the present invention are typically useful for localizing and/or anchoring the conjugated substance to the membranes of a cell. The inherent fluorescence of the cyanine dye portion of the conjugate allows the location of the anchored substance to be determined, and the lipophilic nature of the cyanine retains the substance at that location for further studies. Reactive carbocyanine dyes are useful for preparing conjugates of antibodies or other proteins, thus enabling targeted delivery. These probes also provide a means for attaching enzymes, solid surfaces, toxins, electron-dense visualization reagents and other materials to liposomal membranes.

Selected reactive dyes are also suitable for preparing avidin- or biotin-labeled cyanine dyes. Biotinylated cyanine dyes are useful for coupling avidin conjugates to membranes and liposomes. For example, biotin-phycoerythrin-containing liposomes can be sorted using avidin conjugates. Two-dimensional streptavidin arrays formed at the surface of biotinylated lipid monolayers have been examined by electron microscopy. Additionally, the interaction of biotinylated lipids with streptavidin has been used to provide a model for molecular recognition processes at membrane surfaces.

Staining Samples

The dyes of the present invention are useful for staining any sufficiently lipophilic structure. Examples of lipophilic structures include lipid bilayers (such as cell membranes), natural or artificial liposomes, or any other natural or artificial structure that is sufficiently hydrophobic, such as a lipoprotein. The instant dyes are only dimly fluorescent in aqueous solutions, but exhibit bright fluorescence within cellular membranes, liposomes, or other lipophilic environments. Thus, it is possible to differentiate lipophilic structures from nonlipophilic structures without removing uncomplexed dye.

The dyes of the invention possess particularly advantageous properties for the labeling of biological cells. In addition to the bright fluorescence exhibited in cell membranes, some dyes of the invention do not require the presence of an osmotic regulating agent to achieve suitable loading of cells. In contrast, cell labeling according to the method of Horan et al. is an elaborate and tedious process.

The dyes of the present invention are utilized by preparing a labeling solution of the dye that is combined with a sample for a time sufficient to produce a detectable fluorescence response. Observing or analyzing the pattern of the fluorescence response in the sample gives useful information about the sample.

Selected dyes of the invention can tolerate both fixation and permeabilization conditions. Although the dyes of Horan et al. can tolerate mild fixation condition, permeabilization with acetone almost completely removes them from the cells. The dyes of the invention not only survive this treatment, but in some instances the fluorescent labeling of cells is enhanced by permeabilization with acetone (see FIG. 1).

Finally, the dyes of the invention possess strong absorbance, high fluorescence yields, and substantial photostability (see Tables 2 and 3). By varying the substituents, in particular the number of methine groups, the wavelengths of the absorption and emission bands can be varied to cover the entire visible and near-infrared spectrum.

Preparation of a Labeling Solution

Typically a stock solution is prepared by weighing out a known mass of the pure reagent and dissolving the reagent in an organic solvent. Preferred organic solvents are DMSO, dimethylformamide, a lower alcohol or other completely water-miscible solvents. The stock solutions are protected from light at all times. The labeling solution is prepared by diluting an aliquot of the stock solution into an aqueous buffer or culture medium to the desired labeling concentration.

In general, the amount of dye in the labeling solution is the minimum amount required to yield detectable staining in the sample, without significant background fluorescence or undesired staining of cellular structures. The amount of reagent required for staining cells depends on the number of cells present and the permeability of the cell membrane to the reagent. In the case of staining of tissues, the amount of reagent required may also vary with the accessibility of the reagent to the cells in the tissue. The required concentration for the labeling solution is determined by systematic variation in labeling concentration until a satisfactory level of fluorescent labeling is accomplished. The extent of labeling is typically assessed by microscopy, flow cytometry or fluorometry.

The amount of fluorescent cyanine dye required for staining the cellular membranes of live mammalian cells, is preferably between 0.1 and 20 $\mu$M, more preferably between 1 and 10 $\mu$M. At higher concentrations of stain, background fluorescence or non-specific cellular staining may occur in live cells.

Low concentrations of dye will typically require longer incubation times for equivalent fluorescent brightness to be reached. While the exact concentration of stain to be used is dependent upon the experimental conditions, where the sample cells are incubated at 4° C., dye concentrations between 1 and 20 $\mu$M typically yield good staining with little background fluorescence in 1 to 30 minutes. Alternatively, where the sample cells are incubated at 37° C., dye concentrations between 0.5 and 10 $\mu$M yield good staining in 1 to 30 minutes. For a desired staining result, routine optimization of experimental conditions is required to determine the best concentration of stain to be used in a given application, by methods well known in the art.

Staining the Sample

The sample optionally comprises cells or components thereof, or cell-free liposomes. Typically the sample contains living cells. Any cells can be used, including but not limited to, fresh or cultured cells, cell lines, cells in biological fluids, cells in tissue or biopsy, and yeast cells. Cell components that are suitable for staining include, but are not limited to, lipoproteins, such as low density lipoproteins. Alternatively, the dyes of the invention are used to stain tissues.

Following preparation of the labeling solution, the solution is combined with the sample being analyzed. Most dyes of the invention are membrane permeant and can be introduced into live cells or dead cells, or isolated or artificial liposomes by incubation with the labeling solution. Any other treatment that will permeabilize the plasma membrane, such as electroporation, shock treatments or high extracellular ATP can be used to accelerate introduction of the dye into the cellular cytoplasm. Preferably the dye is introduced into the cell or cells by incubation in the labeling solution.

The dyes of the present invention are generally non-toxic to living cells. Cells that have been incubated in a labeling solution of a dye of the present invention show normal morphology and undergo normal cell division for up to at least 6 days. Where the stained cells have undergone cell division, the resulting daughter cells also possess stained membranes, although with a concomitant loss of fluorescence intensity.

After staining, the cells are optionally treated to fix, and optionally permeabilize, the membranes. A number of fixatives and fixation conditions are suitable for practicing this invention. Useful fixatives include, but are not limited to, formaldehyde, paraformaldehyde, cold methanol, cold ethanol, and 3:1 methanol:acetic acid. Typically, cell fixation is accomplished by incubating in a 3.7% solution of paraformaldehyde for about 15–30 minutes.

Fixation of cells and tissues is optionally followed or accompanied by permeabilization, such as with acetone, ethanol, DMSO or various detergents. Permeabilization is utilized to allow bulky additional detection reagents to enter the cellular space that would ordinarily be impermeant with respect to the cellular membrane. A large variety of fixatives, fixation conditions, and permeabilization agents are known in the art, and other methods of fixing or permeabilizing sample cells in conjunction with the stains of the present invention will be obvious to one of ordinary skill. Unlike previously known cyanine membrane stains, selected embodiments of the present invention exhibit enhanced fluorescent staining after the stained cells have been treated with acetone (as shown in FIG. 1).

Additional Detection Reagents

The use of stains according to the present invention is optionally combined with the use of an additional detection reagent, which is optionally another stain of the invention. An additional detection reagent is a reagent that produces a detectable response due to the presence of a specific cell component, intracellular substance, or cellular condition. One or more additional detection reagents may be used in conjunction with the stains of the present invention, before or after fixation and/or permeabilization. The additional detection reagent may be used to stain the entire cell, or a cellular substructure by selection of an appropriate additional detection reagent with the desired degree of selectivity, such as a labeled antibody, labeled oligonucleotide, or other indicator for a specific cellular component or substructure, e.g. a stain that is selective for the cytoplasm, nucleus, membrane, lysosome, Golgi apparatus, or mitochondria.

The fluorescent signal(s) of the stains of the present invention and the detectable response of the additional detection reagent may be observed simultaneously or sequentially. The observation of membrane staining and a detectable response that are spatially coincident indicate that the additional detection reagent is associated with the cell membranes of the sample. A variety of measurements can be made within cells in this manner, even when the additional detection reagent does not itself localize selectively within the cell membranes.

An additional class of appropriate additional detection reagents is fluorescent nucleic acid stains. A wide variety of appropriate nucleic acid stains are known in the art, including but not limited to, thiazole orange, ethidium homodimer, propidium iodide, Hoechst 33258, and DAPI. Additional useful nucleic acid stains are described in the international applications WO 93/06482, DIMERS OF UNSYMMETRICAL CYANINE DYES (published Apr. 1, 1993); U.S. Pat. No. 5,436,134 to Haugland et al., 1995; U.S. Pat. No. 5,321,130 to Yue et al, 1994; U.S. Pat. No. 5,410,030 to Yue et al., 1995; or U.S. Pat. No. 5,437,980 to Haugland et al., 1995. The use of an appropriate nucleic acid stain in conjunction with the dyes of the present invention can be selected to allow simultaneous observation of nuclear DNA, cellular RNA and/or mitochondrial DNA. Of particular utility is an additional detection reagent that is a cell-permeant nucleic acid stain, such as those described in U.S. Pat. No. 5,436,134, allowing simultaneous visualization of cell membranes and the cellular DNA and RNA, including DNA present in the cell nucleus. Alternatively, the nucleic acid stain used is a stain that is impermeant to live cells and has fluorescence that contrasts with that of the cell or membrane dye used. For green fluorescent stains of the invention, such contrasting stains include propidium iodide and ethidium homodimer, where the red fluorescent nucleus that results from the contrasting stain indicates that the cell membrane is compromised. Similarly, red fluorescent membrane stains can combined with green nuclear stains such as TO-PRO-1, YO-PRO-1, TOTO-1, YOYO-1, or SYTOX dyes (Molecular Probes, Eugene, Oreg.).

Other appropriate additional detection reagents include selected fluorescent pH or metal ion indicators such as those described in U.S. Pat. No. 5,453,517 to Kuhn et al. (1995), or U.S. Pat. No. 5,405,975 to Kuhn et al. (1995); or in Haugland, supra, 1992 HANDBOOK, Sets 20–22 (incorporated by reference).

In another embodiment of the invention, an appropriate additional detection reagent is any probe that selectively stains a cellular organelle such as the cell membrane, nucleus, Golgi apparatus, endoplasmic reticulum, lysosomes, or mitochondria, such as rhodamine 123, or the fixable mitochondrial stains described in U.S. Pat. No. 5,459,268 to Haugland et al. (1995) (hereby incorporated by reference), or another stain of the invention.

Specific examples of additional detection reagents include stains for acidic organelles, such as LYSOTRACKER (Molecular Probes, Eugene, Oreg.) and other stains for lysosomes described in Copending Application STAINS FOR ACIDIC ORGANELLES, by Zhang et al., filed Oct. 17, 1995. The use of stains that are selective for lysosomes in combination with the stains of the present invention allows multiple color visualization of the lipid structures and acidic organelles in cells.

In one embodiment, the additional detection reagent comprises: a) one member of a specific binding pair or a series of specific binding pairs, and b) a means for producing a detectable response. A specific binding pair member can be a ligand or a receptor. Ligands and receptors are complementary members of a specific binding pair, each specific binding pair member having an area on the surface or in a cavity that specifically binds to and is complementary with a particular spatial and polar organization of the other. Ligands for which naturally occurring receptors exist include natural and synthetic peptides and proteins, including avidin and streptavidin, antibodies, enzymes, and hormones; nucleotides and natural or synthetic oligonucleotides; lipids; polysaccharides and carbohydrates; lectins; and a variety of drugs, including therapeutic drugs and drugs of abuse and pesticides.

The additional detection reagent also incorporates a means for producing a detectable response. A detectable response means a change in, or occurrence of, a parameter in a test system that is capable of being perceived, either by direct observation or instrumentally, and that is a function of the presence of a specifically targeted member of a specific binding pair in a cell sample. Such detectable responses include the change in, or appearance of, color, fluorescence, reflectance, pH, chemiluminescence, infrared emission, or the deposition of an electron-rich substrate for visualization by electron microscopy. Appropriate labels to provide a detectable response include, but are not limited to, a visible or fluorescent dye, an enzyme substrate that produces a visible or fluorescent precipitate upon enzyme action (for example, the action of horseradish peroxidase upon diaminobenzidine), visible or fluorescent labeled polymeric microparticles, or a signal that is released by the action of light upon the reagent (e.g. a caged fluorophore that is activated by photolysis, or the action of light upon diaminobenzidine).

The additional detection reagent may be used in conjunction with enzyme conjugates to localize cellular receptors; to localize hybridization probes; or to probe cells and tissues that do not express the enzyme, for example, by enzyme-linked immunosorbent assay (ELISA), or enzyme-mediated histochemistry or cytochemistry, or other enzyme-mediated techniques. Enzyme-mediated techniques take advantage of the attraction between specific binding pairs to detect a variety of analytes. The additional detection reagent optionally comprises an enzyme substrate as the means to produce a fluorescent precipitate in the presence of the appropriate enzyme, as described in U.S. Pat. No. 5,316,906 to Haugland et al. (1994) and U.S. Pat. No. 5,443,986 to Haugland et al. (1995).

Observation/Analysis

At any time after the sample has been stained, the sample is observed with means for detecting the detectable response of fluorescent staining. In one embodiment, observation is accomplished using visible light microscopy, including confocal laser-scanning microscopy. The sample is generally observed immediately after staining is evident. Stained cells are optionally observed after the additional steps of fixation and permeabilization. Observation of the sample requires illuminating the stained sample with a wavelength of light appropriate to generate a fluorescence response.

Optionally, the sample is analyzed using instrumentation. For example, analysis of cells is accomplished by illuminating the stained cells with a wavelength of light appropriate to generate a fluorescence response, and electronically detecting and optionally quantifying the fluorescent emission of the stained cells or liposomes using an appropriate instrument, such as a fluorometer, fluorescent multi-well plate reader, or a flow cytometer. The use of a flow cytometer optionally includes sorting cells based on their fluorescent response.

Any observation or analysis optionally includes the observation or analysis of an additional detection reagent present in the sample, by means generally understood in the art and appropriate for the additional detection reagent utilized.

In one embodiment of the invention, cells stained with the dyes of the invention are observed over time and the changes in fluorescence intensity of the stained cells are related to division or proliferation of the cells. In another embodiment of the invention, cells stained with the dyes of the invention are mixed with unstained cells, either in vivo or in vitro, and the stained cells are sorted from unstained cells. In yet another embodiment of the invention, the sample is a tissue sample that is stained, and the diffusion of the cyanine dye through the tissue is observed. In a specific embodiment the tissue sample is a neuron.

The examples below are given so as to illustrate the practice of this invention. They are not intended to limit or define the entire scope of this invention.

EXAMPLES

Example 1

Synthesis of 3-aminobiphenyl (1):

The following compound is prepared:

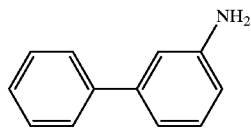

A mixture of 3-nitrobiphenyl (20 g, 100 mmol) and 10% Pd/C (2 g) in MeOH/CHCl$_3$ (300 mL, 1:1) is hydrogenated at 40 psi for 4 hours. The mixture is suction filtered through a layer of diatomaceous earth and washed with MeOH. The filtrate is evaporated to dryness and the solid is further dried under vacuum to give 16 g (95%) of 3-aminobiphenyl.

Example 2

Synthesis of 3-hydrazinobiphenyl hydrochloride (2)

The following compound is prepared:

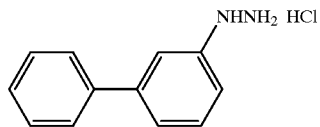

A solution of 3-aminobiphenyl (5 g, 29.6 mmol) is prepared by dissolving the compound in cold CF$_3$CO$_2$H (20 mL). The solution is cooled to 0° C. to give a suspension, and a solution of NaNO$_2$ (2.04 g, 29.6 mmol) in H$_2$O (10 mL) is added dropwise to the suspension with stirring over ½ hour. During the course of the addition, the temperature of the suspension is maintained below 5° C. After the addition is completed, the suspension is allowed to stir an additional 15 min, followed by the addition of SnCl$_2$ (20 g, 88.8 mmol) in concentrated HCl (10 mL). The suspension is vigorously stirred and then diluted with H$_2$O (50 mL). The resulting precipitate is collected by suction filtration and dried under vacuum to give 6 g of crude product, which is used without further purification.

Example 3

Synthesis of 6-phenyl-2,3,3-trimethylindolenine (3)

The following compound is prepared:

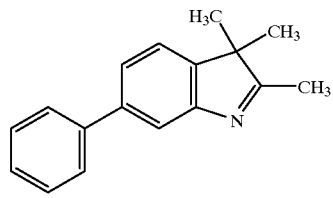

A mixture of 3-hydrazinobiphenyl hydrochloride (72 g, 0.32 mol) and 3-methyl-2-butanone (35 mL, 0.32 mol) in glacial acetic acid (300 mL) is stirred at 110° C. for 1.5 hours. The solution is then cooled to room temperature, and filtered to remove the insoluble ammonium chloride salt. The filtrate is concentrated to ⅓ of its volume and then poured into H$_2$O (1 L). The product is extracted with EtOAc (4×200 mL). The combined EtOAc solution is neutralized with saturated NaHCO$_3$ and washed with H$_2$O (200 mL) and brine (200 mL). After drying over anhydrous Na$_2$SO$_4$, removal of solvent gives 20 g of brown oil. The product is further purified by vacuum distillation.

Example 4

Synthesis of 3,3-dimethyl-2-methylene-1-octadecyl-6-phenylindoline (4)

The following compound is prepared:

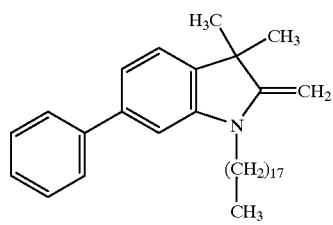

A mixture of compound 3 (5.18 g, 22.0 mmol) and octadecyl p-chlorobenzenesulfonate (9.8 g, 22.0 mmol) is heated at 120–130° C. for 24 hours. The resulting gummy mixture is cooled to room temperature and then dissolved in EtOAc (500 mL). The solution is washed with saturated NaHCO$_3$ (3×200 mL) and then brine (100 mL). The solution is dried with anhydrous Na$_2$SO$_4$ and evaporated to give a dark brown oil, which is purified by a silica gel column chromatography using CHCl$_3$/MeOH (10:0.1) as the eluting solvent. Yield: 41%.

Example 5
Synthesis of 1,1'-dioctadecyl-6,6'-diphenyl-3,3,3',3'-tetramethylindocarbocyanine, chloride salt (5)
The following compound is prepared:

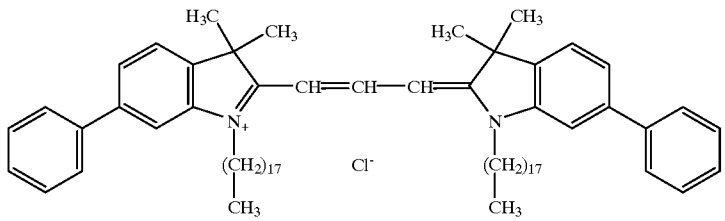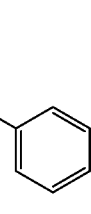

Compound 4 (7.31 g, 15 mmol) and CF$_3$CO$_2$H (1.16 mL, 15 mmol) are combined with dry pyridine (90 mL) and then heated to reflux. Triethylorthoformate (9.98 mL, 60.0 mmol) is added dropwise over a period of 45–50 min. The solution is allowed to reflux for another hour. The reaction is cooled to room temperature and then poured into a solution of 1 L brine and 1 L H$_2$O. The mixture is stirred by hand with a glass rod until the oily material has been transformed into a dark red precipitate. The precipitate is filtered, washed with water several times and then dried in a vacuum oven. The crude product is purified by chromatography on a silica gel column using MeOH in 1:1 EtOAc/CHCl$_3$ as the eluting solvent. Yield: 50%.

Example 6
Synthesis of 1,1'-dioctadecyl-6,6'-di(4-sulfophenyl)-3,3,3',3'-tetramethylindocarbocyanine (6)
The following compound is prepared:

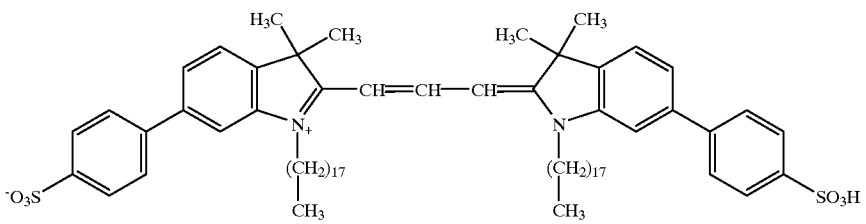

Compound 5 (3.5 g, 3.4 mmol) is dissolved with stirring in about 50 mL conc H$_2$SO$_4$ at room temperature. The yellow brown solution is cooled and stirred at 0° C. About 20 mL 20% fuming H$_2$SO$_4$, which has cooled to 0° C., is added dropwise with a pipet to the above solution over 15–20 min. At the end of the reaction the dark brown solution is carefully poured over crushed ice (200 g). The red precipitate is suction filtered and washed with water several times, followed by drying. The crude product is purified by running a short silica gel column using MeOH/CHCl$_3$ as the eluting solvent. The product is further purified by briefly boiling a suspension of the product in MeOH, followed by cooling and filtration. After drying, about 1.5 g of pure product is obtained.

Example 7
Synthesis of 2-methylene-3-octadecyl-5-phenylbenzoxazole (7):

The following compound is prepared:

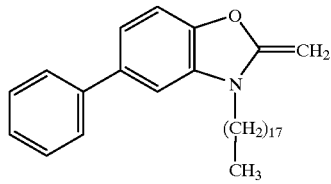

Powdered 1-octadecanol (15.4 g, 56.9 mmol) and diisopropylethylamine (9.9 mL, 56.9 mmol) are dissolved in 200 mL CHCl$_3$ (dried over molecular sieves). To the above stirred solution is added trifluoromethanesulfonic anhydride (10.4 mL) dropwise over a period of 1 hours. Powdered 5-phenylbenzoxazole (16.7 g, 79.7 mmol) is then added portion-wise over a period of 10 minutes. After stirring overnight, the solution is washed with water and dried with anhydrous Na$_2$SO$_4$. The solution is loaded onto a large silica column and eluted with MeOH/CHCl$_3$. The product is obtained as a colorless solid (20 g, 77%).

Example 8

Synthesis of 3,3'-dioctadecyl-5,5'-diphenyloxacarbocyanine chloride (8)

The following compound is prepared:

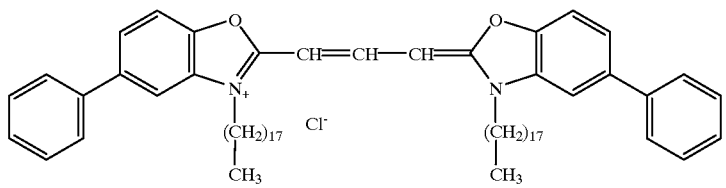

Compound 7 (8 g, 17.4 mmol) is dissolved in approximately 60 mL pyridine (dried over KOH), followed by the careful addition of 6 mL trifluoroacetic acid. After heating to reflux, triethylorthoformate (20 mL, 120 mmol) is added dropwise over a period of 2 hours. The solution is refluxed an additional 4 hours. The hot solution is poured over a solution of 1 L of water and 1 L of brine. The resulting mixture is stirred until the oily material becomes a yellow precipitate. The precipitate is filtered and washed several times with water. To ensure complete ion exchange, the solid is redissolved in a minimum of DMF and the solution is poured into 1 L of brine. The precipitate is collected by suction filtration and washed with water, followed by drying in a vacuum oven at 50° C. for 24 hours. The product is purified by chromatography on a silica gel column eluting with MeOH/CHCl$_3$. The product is obtained as a yellow orange solid (5 g, 59%).

Example 9

Synthesis of 1-octadecyl-2,3,3-trimethylindoleninium p-chlorobenzenesulfonate (9)

The following compound is prepared:

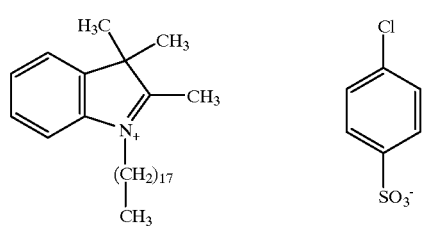

A mixture of 2,3,3-trimethylindolenine (15.9 g, 0.1 mol) and octadecyl p-chlorobenzenesulfonate (44.5 g, 0.1 mol) is heated at 120° C. for 24 hours. The dark red gummy solid is triturated with hexane and then suction filtered. The solid is recrystallized from EtOAc to give a colorless solid (40 g, 66%).

Example 10

Synthesis of 1-octadecyl-5-sulfonato-2,3,3-trimethylindolininium (10)

The following compound is prepared:

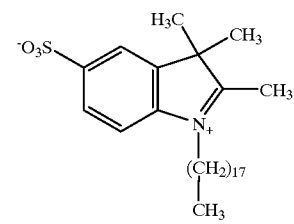

To a mechanically stirred solution of 20% fuming H$_2$SO$_4$ (100 mL), cooled in an ice-water bath, is added Compound 9 (20 g, 33 mmol) portion wise over a period of 1 hour. The solution is continued to stir for an additional 45 minutes, and then carefully poured over crushed ice. The resulting precipitate is collected by suction filtration while the mixture is still cold. The precipitate is washed with ether and then dried under vacuum at 40° C. for three days to give a colorless solid (6 g, 34%).

Example 11

Synthesis of 1,1'-dioctadecyl-5,5'-disulfo-3,3,3',3'-tetramethylindocarbocyanine (11)

The following compound is prepared:

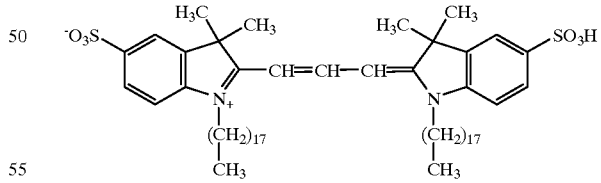

To a refluxing solution of 10 (1.5 g, 1.39 mmol) in pyridine (30 mL) is added triethylorthoformate (2 mL, 12.2 mmol) dropwise over a period of 30 minutes. The solution is allowed to stir for an additional three hours. The solution is cooled to room temperature and then poured into ether (100 mL). The resulting precipitate is collected by suction filtration. The crude product is purified by column chromatography over silica gel eluting with MeOH/CHCl$_3$ to give 0.83 g (60%) of 11 as a dark red solid.

Example 12

Synthesis of 1,1'-dioctadecyl-5,5'-disulfo-3,3,3',3'-tetramethylindodicarbocyanine (12)

The following compound is prepared:

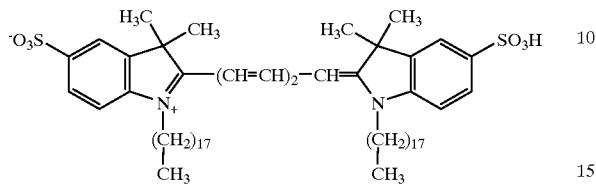

To a boiling solution of 10 (1.0 g, 0.93 mmol) in pyridine (20 mL) is added portion wise 1,1,3,3-tetramethoxypropane (1.5 mL, 9.3 mmol) over the course of 1 hour. After two hours at reflux, the reaction is cooled to room temperature. Diethyl ether (80 mL) is added. The resulting precipitate is collected using vacuum filtration. The product is purified by column chromatography on silica gel eluting with methanol/chloroform.

Example 13

Synthesis of 5-(phthalimidomethyl)indolenine (13)

The following compound is prepared:

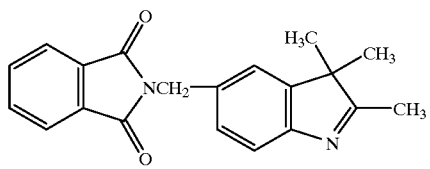

To a solution of 2,3,3-trimethylindolenine (2.06 g, 12.9 mmol) in conc $H_2SO_4$ (20 mL) is added in small portions N-hydroxymethylphthalimide (2.29 g, 12.9 mmol) over a period of ½ h. The brown solution is stirred at room temperature overnight and then poured over crushed ice. The pH of the mixture is adjusted to about 8 by the addition of $NH_4OH$. The precipitate is collected by suction filtration and washed with water, followed by drying in a vacuum oven to give 13 in quantitative yield.

Example 14
Synthesis of 1-octadecyl-5-(phthalimidomethyl)-2,3,3-trimethylindolininium. p-chlorobenzenesulfonate (14)

The following compound is prepared:

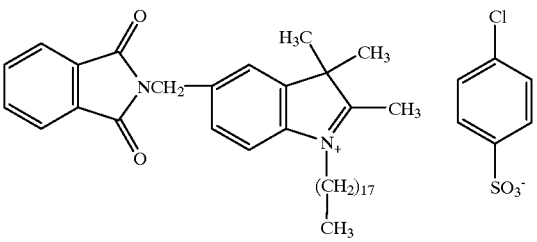

A mixture of compound 13 (4.2 g, 13.2 mmol) and octadecyl p-chlorobenzenesulfonate (6.0 g, 13.2 mmol) is heated at 120° C. for 24 h. At the end of the reaction, EtOAc (100 mL) is added and the mixture is heated at reflux until a homogeneous solution is formed. Crystals of the product form as the solution is cooled to room temperature. The crystals are collected by suction filtration and washed with EtOAc and hexane, followed by drying in a vacuum oven. The product is obtained as colorless crystals (7 g, 70%).

Example 15

Synthesis of 1,1'-dioctadecyl-5-(phthalimidomethyl) indocarbocyanine chloride (15)

The following compound is prepared:

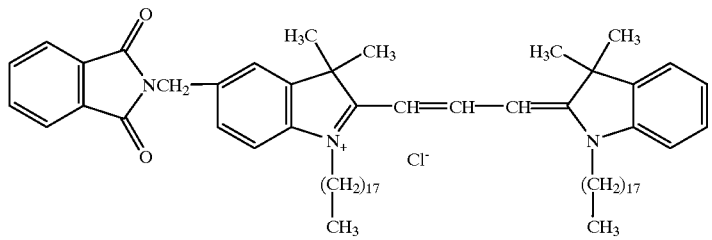

A mixture of 9 (2.6 g, 4.31 mmol) and N,N'-diphenylformamidine (0.93 g, 4.74 mmol) is suspended in 15 mL of acetic anhydride. The suspension is sonicated for approximately 10 minutes and then stirred overnight. The solvent is removed by vacuum distillation at room temperature. The resulting oily residue is further dried under vacuum to remove the remaining solvent. To the gummy solid is added 14 (3.2 g, 4.2 mmol) and pyridine (20 mL). The mixture is heated at reflux for about 1 h. The dark red solution is cooled to room temperature and is then poured into saturated NaCl (200 mL). After standing overnight, the supernatant liquid is decanted and the precipitated solid is washed with water and dried. The crude product is purified by column chromatography on silica gel using MeOH in 1:1 EtOAc/$CHCl_3$ as the eluting solvent. The product is obtained as a dark red solid (70%).

Example 16
Synthesis of 5-aminomethyl-1,1'-dioctadecyl-3,3,3',3'-tetramethylindocarbocyanine chloride (16)

The following compound is prepared:

Compound 15 (2.10 g, 2.04 mmol) is dissolved in approximately 100 mL MeOH, followed by the addition of 1 mL hydrazine hydrate. The solution is stirred at room temperature for 24 hours. The solvent is removed and the crude product is purified using column chromatography on silica gel eluting with MeOH/CHCl$_3$.

Example 17
Synthesis of 5-(((4-chloromethyl)benzoyl)amino)methyl)-1,1'-dioctadecyl-3,3,3',3'-tetramethylindocarbocyanine chloride (17)
The following compound is prepared:

To 16 (600 mg, 0.67 mmol) in 10 mL chloroform is added triethylamine (100 mg, 1.0 mmol). 4-Chloromethylbenzoyl chloride (190 mg, 1.0 mmol) in 2 mL chloroform is added dropwise. After 15 min of stirring at room temperature, the solution is washed with water and then brine. The organic layer is concentrated and then subjected to column chromatography on silica gel using MeOH/CHCl$_3$ to give 17 (Yield=90%).

Example 18
Synthesis of methyl 4-hydrazinophenylacetate hydrochloride (18)
The following compound is prepared:

To a solution of methyl 4-aminophenylacetate (5.5 g, 33.3 mmol) in concentrated HCl (35 mL) at 0° C. is added a solution of NaNO$_2$ (2.3 g, 33.3 mmol) in water (10 mL). The temperature of the reaction is maintained at 0–5° C. After stirring for 30 minutes, a solution of SnCl$_2$ (19 g, 99.9 mmol) in concentrated HCl (10 mL) is added and the mixture is vigorously stirred with a stirring rod. The mixture is then diluted with water (50 mL), and the resulting precipitate is collected by suction filtration and washed with water. The solid is dried under vacuum to give 5 g of 18, which is used without further purification.

Example 19
Synthesis of 5-methoxycarbonylmethyl-2,3,3-trimethylindolenine (19)
The following compound is prepared:

To a slurry of Compound 18 (20.5 g, 95.6 mmol) suspended in acetic acid (100 mL) is added 3-methylbutanone (10.5 mL, 95.6 mmol). The mixture is heated at reflux for 2 hours. The solution is then cooled to room temperature and the solvent removed by rotary evaporation. The remaining slurry is poured into water and the pH is adjusted to 7–8 by adding Na$_2$CO$_3$. The product is extracted with ethyl acetate three times (3×100 mL). The combined organic layers are washed with water and then brine, followed by drying over anhydrous sodium sulfate. Removal of solvent gives crude 19 as a brown oil, which is further purified using column chromatography on silica eluting with EtOAc/hexane. Yield: 80%.

Example 20
Synthesis of 5-methoxycarbonylmethyl-1-octadecyl-2,3,3-trimethylindoleninium p-chlorobenzenesulfonate (20)
The following compound is prepared:

Compound 20 is synthesized from Compound 19 and octadecyl p-chlorobenzenesulfonate using the procedure described in Example 4.

Example 21
Synthesis of 1,1'-dioctadecyl-5-methoxycarbonylmethyl-3,3,3',3'-tetramethylindocarbocyanine p-chlorobenzenesulfonate (21)
The following compound is prepared:

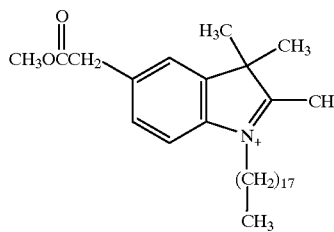 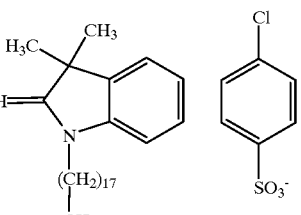

Compound 21 is synthesized from Compound 20 using the procedure described in Example 15.

Example 22
Synthesis of 5-carboxymethyl-1,1'-dioctadecyl-3,3,3',3'-tetramethylindocarbocyanine (22)
The following compound is prepared:

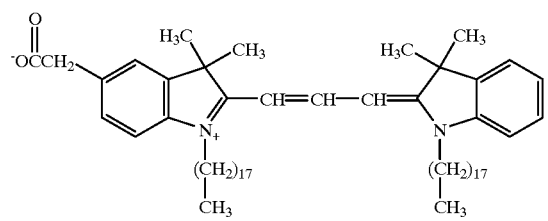

To a solution of 21 (0.5 g) in a 1:1 mixture of MeOH and THF is added a solution of LiOH (0.2 g) in 10 mL $H_2O$. The solution is stirred at room temperature for 24 hours. The organic solvent is removed via rotary evaporation. To the remaining mixture is added 3 M HCl until the pH is 7. The dark red precipitate is collected by suction filtration and then dried at 50° C. under vacuum for 24 hours. The product is further purified using column chromatography on silica gel eluting with $MeOH/CHCl_3$.

Example 23
Synthesis of an indocarbocyanine with a succinimidyl ester (23)
The following compound is prepared:

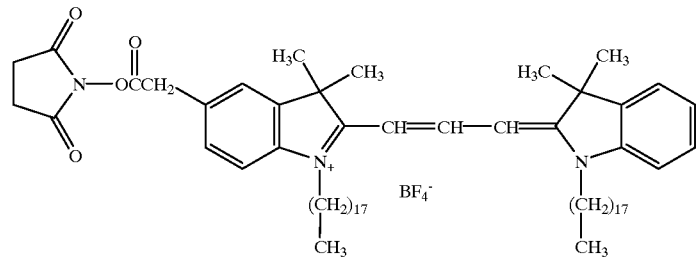

To a solution of 22 (100 mg, 0.11 mmol) in 5 mL DMF is added triethylamine (11 mg, 0.11 mmol) and 2-succinimidyl-1,1,3,3-tetramethyluronium tetrafluoroborate (34 mg, 0.11 mmol). The solution is stirred for 2 hours and then poured into water (20 mL). The resulting precipitate is collected by suction filtration and then dried at room temperature under high vacuum.

Example 24
Synthesis of an indocarbocyanine with an acid chloride group (24)
The following compound is prepared:

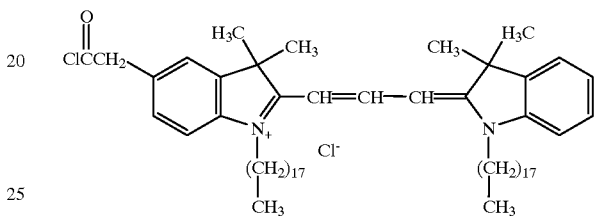

To a stirred solution of 22 (100 mg, 0.11 mmol) in 5 mL dry $CH_2Cl_2$ under nitrogen is added oxalyl chloride (70 mg, 0.55 mmol) dropwise. The solution is stirred for 3 hours at room temperature. The solvent and unreacted oxalyl chloride are removed by rotary evaporation to give Compound 24 as a gummy solid.

Example 25
Synthesis of an oxacarbocyanine with two sulfonyl chloride groups (25)
The following compound is prepared:

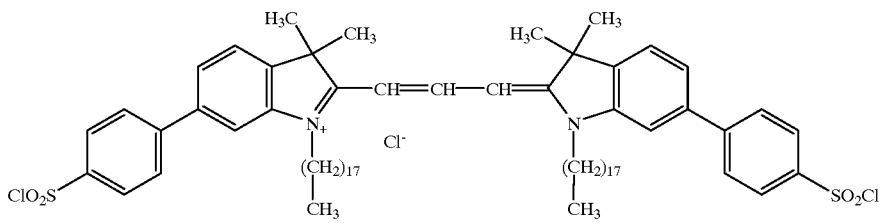  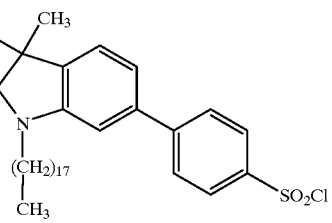

To a stirred solution of Compound 8 (100 mg) in 5 mL DMF at 0° C. under nitrogen is added dropwise a large excess (0.2 mL) of thionyl chloride. After the addition is completed, the solution is stirred at room temperature for an additional 2 hours. The solution is then poured into crushed ice (20 g). The resulting precipitate is collected by suction filtration and dried at room temperature under high vacuum for 24 hours.

Example 26
Synthesis of 3,3-dimethyl-2-methylene-5-nitro-1-octadecylindoline (26)
The following compound is prepared:

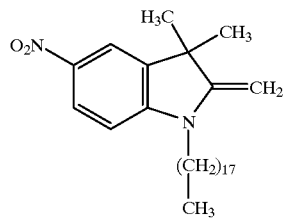

To a stirred solution of Compound 9 (2.0 g, 3.31 mmol) in 15 mL concentrated sulfuric acid at 0° C. is added powdered NaNO₃ (0.28 g, 3.31 mmol) portion-wise over a period of 20 min. The solution is stirred at 0° C. for an additional 30 minutes, and then at room temperature for 3 hours. The resulting solution is poured into crushed ice (50 g). NaCl is added to the solution until it is saturated. The solution is then extracted with chloroform three times (3×50 mL). The organic fractions are combined and washed with water (50 mL), saturated Na₂CO₃ (50 mL) and water (50 mL) again, followed by drying over anhydrous sodium sulfate. The solvent is removed by rotary evaporation to give Compound 26 as a gummy solid. The product is further purified using column chromatography on silica gel eluting with EtOAc/Hexane.

Example 27
Synthesis of an unsymmetrical cyanine having a nitro substituent (27)
The following compound is prepared:

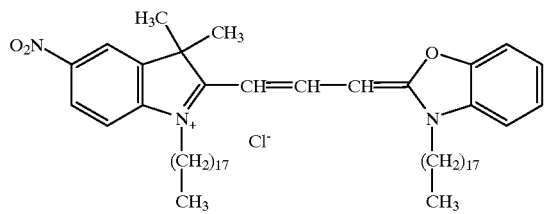

A mixture of Compound 26 (2 g, 4.39 mmol) and N,N'-diphenylformamidine (0.86 g, 4.39 mmol) in 15 mL acetic anhydride is stirred at room temperature for 24 hours. The solvent is removed by vacuum distillation at room temperature to give a gummy residue. The residue is redissolved in 30 mL pyridine, followed by the addition of 2-methyl-1-octadecylbenzoxazolium p-chlorobenzenesulfonate. The solution is heated at reflux for 2 hours and then poured into saturated sodium chloride solution. The resulting precipitate is collected by suction filtration and dried at 50° C. under vacuum for 24 hours. The product is further purified using column chromatography on silica gel eluting with MeOH/CHCl₃.

Example 28
Synthesis of a cyanine dye having an amino substituent (28)
The following compound is prepared:

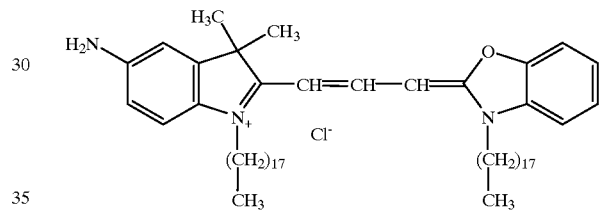

A mixture of Compound 27 (0.5 g, 0.56 mmol) and SnCl₂.2H₂O (0.38 g, 1.68 mmol) in 20 mL ethanol is stirred at 70° C. for 2 hours. The solvent is removed by rotary evaporation and the solid is subjected to column chromatography eluting with MeOH/CHCl₃ to give Compound 27 as a red solid.

Example 29
Synthesis of a cyanine having an isothiocyanate substituent (29)
The following compound is prepared:

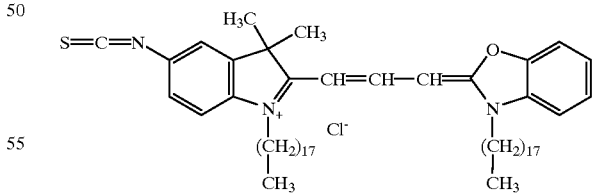

To a stirred solution of Compound 28 (100 mg, 0.12 mmol) in 10 mL dry acetonitrile at 0° C. under nitrogen is added dropwise thiophosgene (15 mg, 0.13 mmol). The resulting solution is warmed to room temperature and stirred for two hours. The solvent is removed by rotary evaporation to give a gummy solid residue. The solid is redissolved in methylene chloride and precipitated by addition of hexane. The precipitate is collected by suction filtration and dried under high vacuum at room temperature.

Example 30
Synthesis of a cyanine dye having a maleimidyl substituent (30)

The following compound is prepared:

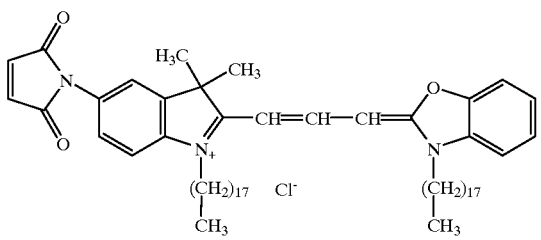

To a stirred solution of Compound 28 (100 mg, 0.12 mmol) in methylene chloride (15 mL) is added maleic anhydride (17.6 mg, 0.18 mmol). The resulting solution is stirred at room temperature for 24 hours. The solution is then diluted with an additional 20 mL methylene chloride and washed with water and brine, in that order. After the organic layer is dried over anhydrous sodium sulfate, the solvent is removed by rotary evaporation. The resulting solid is suspended in acetic anhydride (10 mL) and sodium acetate (9.8 mg, 0.12 mmol) is added. The mixture is heated at reflux for approximately two minutes, and then cooled to room temperature. The solvent is removed under high vacuum at room temperature. The solid is dissolved in chloroform (30 mL) and washed with water and brine. The organic layer is evaporated to dryness to give 30 as a gummy solid, which is further purified using column chromatography on silica gel eluting with MeOH/CHCl$_3$.

Example 31
Synthesis of an indocarbocyanine dye having a cyclic ring substituent in the polymethine bridge (31)

The following compound is prepared:

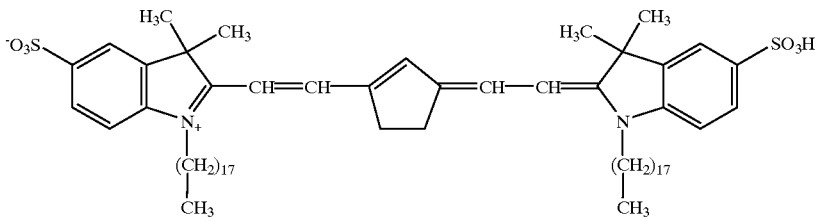

A 2:1 mixture of Compound 10 and (5-phenylamino-2,4-dimethylene-2,4-pentadienylidene)phenylammonium chloride (Makin et al., ZH. ORG. KHIM. 13, 2440 (1977)) is dissolved in a mixed solvent of pyridine and acetic anhydride (1:1). The resulting solution is heated at reflux for approximately 2 hours, and then cooled to room temperature. The solvent is removed using rotary evaporation. The resulting solid is triturated using a minimum amount of water, and then collected using suction filtration. The product is purified using column chromatography.

Example 32
Preparation and culture of cells.

Human lymphoid B-cell lines (LCLs) are derived from peripheral blood lymphocytes by Epstein-Barr virus transformation according to standard procedures. Human LCLs are cultured in RPMI 1640 medium supplemented with 10% FBS, 100 U penicillin, 100 μg streptomycin and 300 μg L-glutamine per mL of culture medium at 37° C. in a humidified atmosphere of 5% CO$_2$ in air. Cells are kept in logarithmic growth by regularly diluting cell cultures with fresh culture medium. Adherent cells are cultured on an appropriate surface, such as a cell culture flask, cell culture dish or a coverslip, in a suitable culture medium at 37° C. in a humidified atmosphere of 5% CO$_2$ in air. Cells are passaged by trypsinization according to the standard methods known in the art.

Example 33
Labeling of cells.

To a sample suspension of cells or liposomes, a labeling solution of a dye of the present invention is added in an amount sufficient to obtain a dye concentration of 2 to 20 μM. The sample is then incubated at 37° C. for a time sufficient to give clearly detectable staining of the cells. The stained cells are collected by centrifugation, and resuspended into phosphate buffered saline. This step is repeated once. The stained cells are either fixed, are examined directly, or are processed for further experimentation.

Example 34
Detection of fluorescently labeled cells.

Labeled cells are viewed with a microscope equipped with an excitation source suitable to excite the selected cyanine dye. Alternatively, suspensions of labeled cells are analyzed with a flow cytometer equipped with a laser or other source of excitation light emitting at an appropriate wavelength. The resulting fluorescence emission is monitored with systems of filters and dichroic mirrors.

Example 35
Retention of dye in stained cells.

The sample cells are labeled and washed free of dye according to Example 33, and then mixed with a similar number of unstained cells in an appropriate cell culture medium. The mixture of cells is then incubated at 37° C. After 1, 2, 3, and 4 hours of incubation, respectively, samples are taken, and analyzed with a flow cytometer.

No decrease in fluorescence intensity is observed with any of the dyes. The initially unstained cells mixed with the stained cell do NOT show an increase in fluorescence intensity, showing that there is no transfer of stain from initially stained to unstained cells. No loss of staining is observed throughout a 4 hour time period.

Example 36
Fixation/Permeabilization of stained cells.

Sample cells are stained according to Example 33, centrifuged, and the cell pellet is resuspended into 3.7% formaldehyde diluted into phosphate buffered saline at 37° C. The sample cells are incubated in formaldehyde at room temperature for at least 15 minutes, then centrifuged, and the cell pellet is resuspended into phosphate buffered saline at room temperature, and maintained there for an additional 15 minutes. The sample cells are then analyzed immediately using a device as said in Example 34. Alternatively, the fixed sample cells are exposed to a secondary reagent, such as, but not limited to, an antibody, or an additional cellular stain, and then analyzed.

Similarly, the fixed cells are optionally treated with acetone at −20° C. to permeabilize the cell membranes.

Sample cells thus treated with acetone are then treated with phosphate buffered saline for at least 15 minutes. The sample cells are then analyzed with a device as described in Example 34, or exposed to a secondary reagent. The fixed and permeabilized cells are applied to a coverslip or equivalent surface, and are then air dried and mounted in an acrylic mounting medium to make a permanent sample.

Alternatively, stained sample cells are treated with acetone at −20° C., treated with phosphate buffered saline as outlined above, and submitted to further analysis such as, but not limited to, detection of enzymatic activity with chromogenic or fluorogenic substrates. Cells thus treated are then analyzed with a device as outlined in Example 34. The effect of fixation and permeabilization on fluorescence intensity of the stained cells is shown in FIG. 1.

Example 37

Time resolved assay of cellular fluorescence decay in cell culture.

An aliquot of a cell culture is stained as in Example 33. The stained cells are then washed free of dye by centrifugation, and resuspended into phosphate buffered saline. This step is repeated once. The sample cells are then resupended into fresh culture medium and plated in suitable cell culture flasks or dishes, and maintained protected from light in a suitable incubator at 37° C. An aliquot of the initial cell culture is frozen immediately in culture medium and kept at −20° C. in the dark.

After a sufficiently long interval of cell culture (typically 6 to 24 hours), an aliquot of the cell culture is taken. Cells are either harvested by trypsinization or by sampling from a suspension cell culture. Cells are resuspended in fresh cell culture medium, and either frozen as described above, or analyzed with the aid of a flow cytometer. Optionally, sample cells are counterstained for at least 30 minutes at 37° C. with a 10 μM solution of the membrane-permeable DNA stain Hoechst 33342. Light from the Hoechst 33342 stained cells is recorded with a system of filters and dichroic mirrors suitable to collect light in the region of 400 to 500 nm. This dual parameter analysis system resolves cells according to the G1, S and G2 phase of the cell cycle. To allow for correction of small day-to-day variation in the settings of the flow cytometer a small sample of fluorescent polymeric microspheres of known fluorescence intensity is added to each cell sample to be analyzed. This assay is repeated for the duration of the cell proliferation evaluation period at equally spaced time intervals for at least 6 times. The fluorescence intensity decay for the dyes of the present invention as a function of time is fitted assuming a single exponential component. The fluorescence decay constant thus obtained is the inverse of the cell division rate, if an exponential increase in cell number can be assumed. All fluorescence intensities are relative to those of cells stained, but not further cultured.

Example 38

Liposome preparation and staining.

Figure 2:
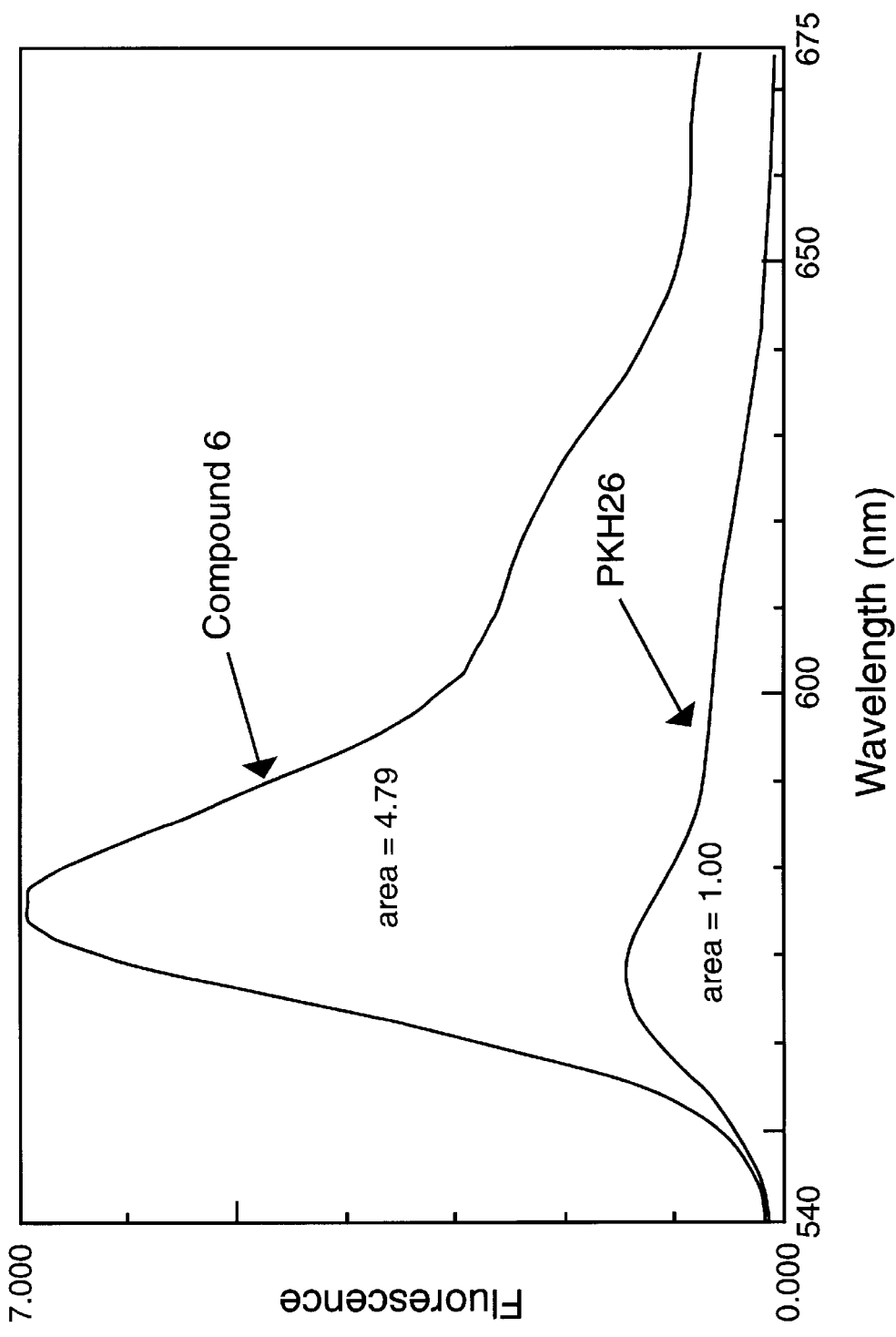
FIG. 2: A comparison of fluorescence emission spectra of PKH26 and Compound 6 in liposomes suspended in pH 7.4 phosphate buffer (prepared as in Example 38). The dyes are excited at 530 nm and the optical density is set at 0.02. The area under each curve represents the relative fluorescence quantum yield of the dyes, normalized relative to PKH26.
Figure 3:
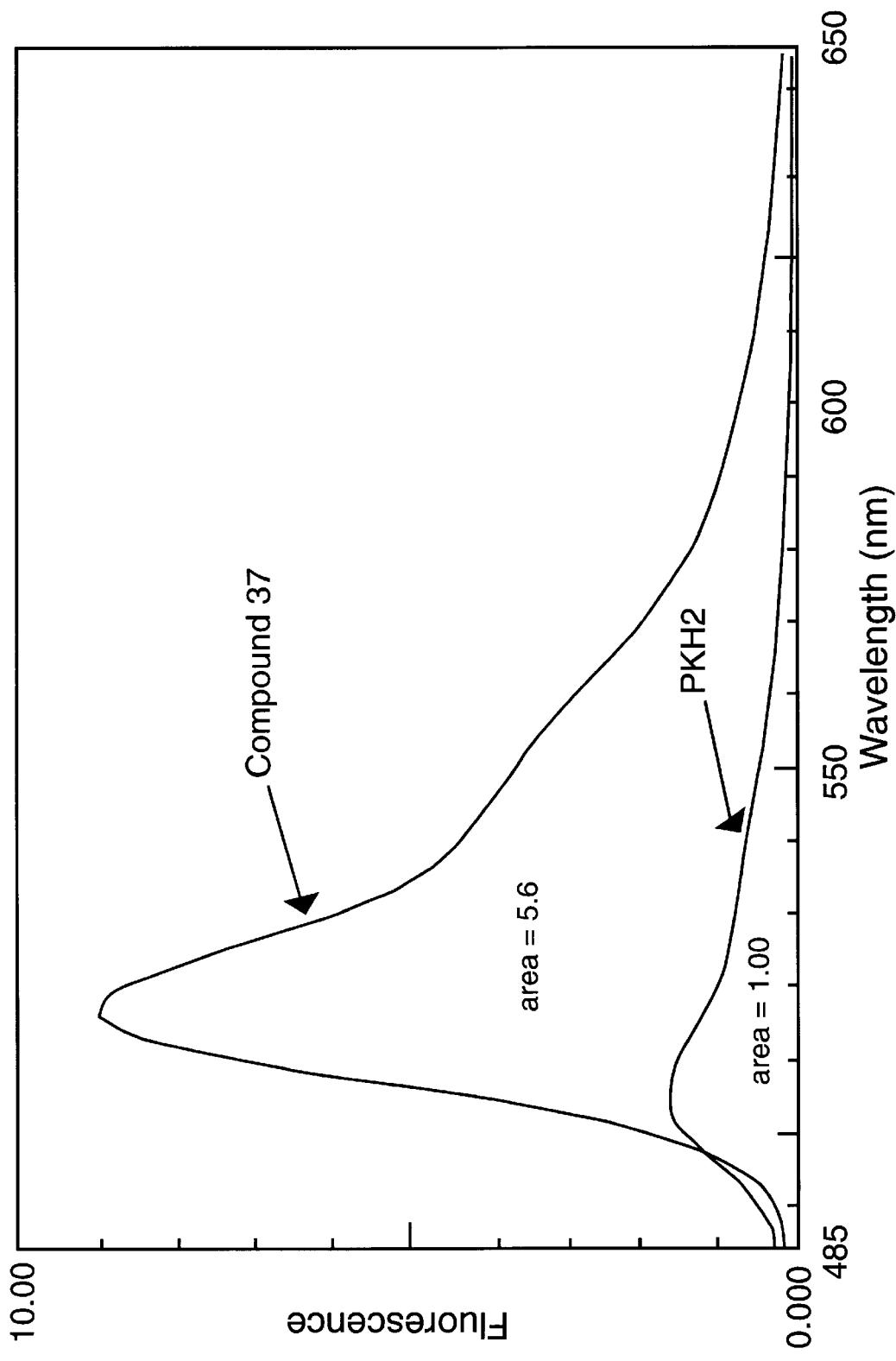
FIG. 3: A comparison of fluorescence emission spectra of the commercially available cyanine dye PKH2 (Sigma Chemical Co., St. Louis, Mo.) and Compound 37 in liposomes suspended in pH 7.4 phosphate buffer (prepared as in Example 38). The dyes are excited at 475 nm and the optical density is set at 0.02. The area under each curve represents the relative fluorescence quantum yield of the dyes, normalized relative to PKH2.
Figure 4:
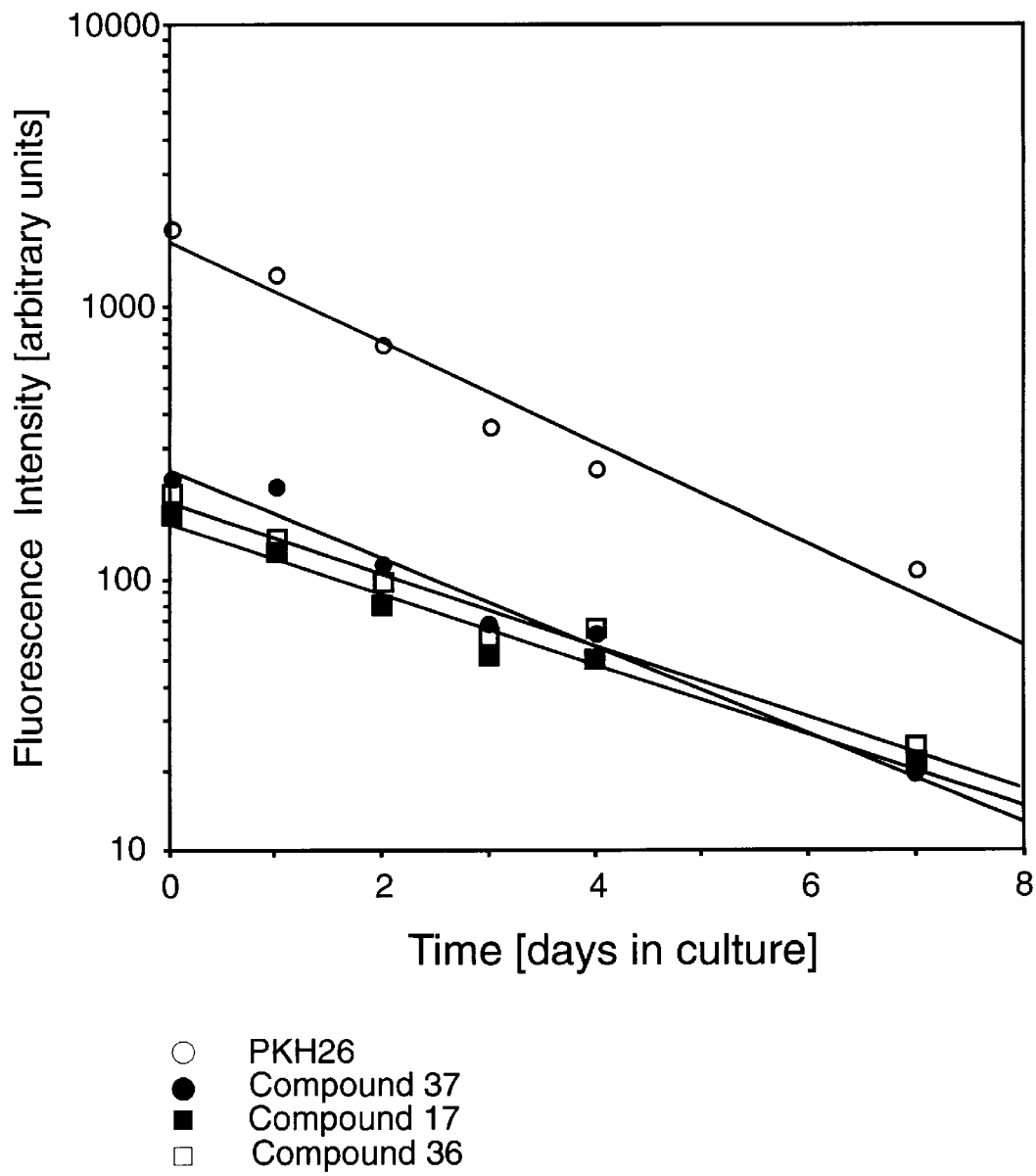
FIG. 4: A depiction of the results of a time-resolved assay of cellular fluorescence decay in cell cultures, as described in Example 37. Fluorescence decay with cell division is shown with cells stained with PKH 26 and Compounds 37, 17 and 36.

DOPC liposomes are prepared by the addition of 100 μL of 40 mM DOPC in EtOH over 1 min to 10 mL of 50 mM pH 7.4 phosphate buffer with stirring. A DMSO solution of the desired dye of the invention is added to the liposome solution so that the final dye to DOPC ratio is about 1:400. Spectra of stained liposome suspensions are given in FIGS. 2 and 3.

It is to be understood that, while the foregoing invention has been described in detail by way of illustration and example, numerous modifications, substitutions, and alterations are possible without departing from the spirit and scope of the invention as described in the following claims.

What is claimed is:

1. A compound having the formula

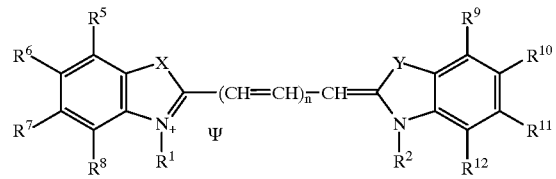

wherein $R^1$ and $R^2$ are independently linear or branched hydrocarbons having 7–30 carbons, where each hydrocarbon group optionally incorporates a 5- or 6-membered unsaturated hydrocarbon ring, and each hydrocarbon is independently and optionally substituted one or more times by F, Cl, or alkoxy having 1–6 carbons;

X and Y are independently O, S or $CR^3R^4$, where $R^3$ and $R^4$, which may be the same or different, are independently alkyl groups having 1–6 carbons, or $R^3$ and $R^4$ taken in combination complete a five or six membered saturated ring;

n=0–3, yielding a methine bridge that is unsubstituted or is optionally substituted by F, Cl or alkyl having 1–6 carbons; or any double bond in the methine bridge is optionally incorporated into a 5- or 6- membered hydrocarbons ring that is unsubstituted or is optionally substituted one or more times by alkyl having 1–6 carbons;

$R^5$, $R^6$, $R^7$ $R^8$, $R^9$, $R^{10}$, $R^{11}$ and $R^{12}$ are independently hydrogen, F, Cl, Br, I, CN, sulfo, phenyl, sulfophenyl, polysulfophenyl, carboxy, amino, ammonium, or an alkyl group having 1–22 carbons that is optionally and independently substituted by one or more of F, Cl, or —$OR^{13}$ where $R^{13}$ is H or an alkyl group having 1–6 carbons; or any two adjacent substituents of $R^5$, $R^6$, $R^7$, $R^8$, $R^9$, $R^{10}$, $R^{11}$ and $R^{12}$, when taken in combination, form a single fused benzo substituent; or any of $R^5$, $R^6$, $R^7$, $R^8$, $R^9$, $R^{10}$, $R^{11}$ and $R^{12}$ is a methylbenzamido, chloromethylbenzamido, maleimidyl benzamido, maleimidyl alkylamido, azidobenzamido or azidoperfluorobenzamido;

Ψ is a biologically compatible counterion, if necessary;

provided that at least one of $R^5$, $R^6$, $R^7$, $R^8$, $R^9$, $R^{10}$, $R^{11}$ or $R^{12}$ is a methylbenzamido, chloromethylbenzamido, maleimidyl benzamido, maleimidyl alkylamido, azidobenzamido or azidoperfluorobenzamido, and no more than one of $R^5$, $R^6$, $R^7$ and $R^8$, and no more than one of $R^9$, $R^{10}$, $R^{11}$ or $R^{12}$ is a methylbenzamido, chloromethylbenzamido, maleimidyl benzamido, maleimidyl alkylamido, azidobenzamido or azidoperfluorobenzamido.

2. A compound, as claimed in claim 1 wherein at least one of $R^5$, $R^6$, $R^7$, $R^8$, $R^9$, $R^{10}$, $R^{11}$ or $R^{12}$ is maleimidyl benzamido, maleimidyl alkylamido, azidobenzamido or azidoperfluorobenzamido.

3. A compound, as claimed in claim 1, wherein X and Y are each $CR^3R^4$ or O.

4. A compound, as claimed in claim 1, wherein both $R^1$ and $R^2$ are linear, saturated or unsaturated hydrocarbons that have 12–22 carbons.

5. A compound, as claimed in claim 4, wherein n=1 or 2.

6. A compound, as claimed in claim 1, wherein

X and Y are each $CR^3R^4$ or O;

the methine bridge is unsubstituted, and n=1 or 2;
and at least one of $R^6$, $R^7$, $R^{10}$ and $R^{11}$ is a methylbenzamido or a chloromethylbenzamido.

7. A compound, as claimed in claim 1, having the formula

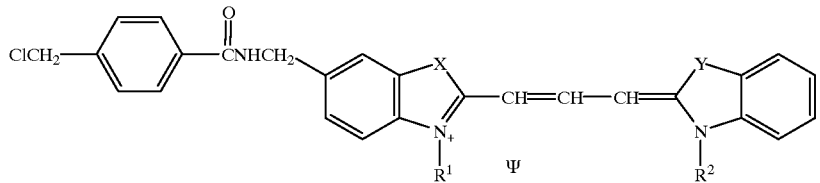

or the formula

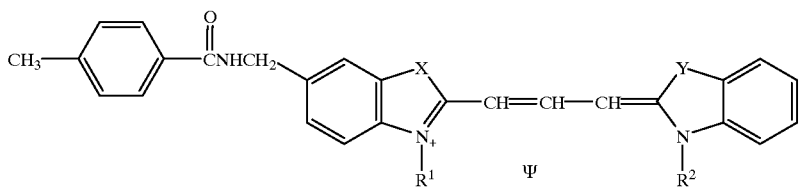

wherein X and Y are each $CR^3R^4$ or O.

8. A compound having the formula

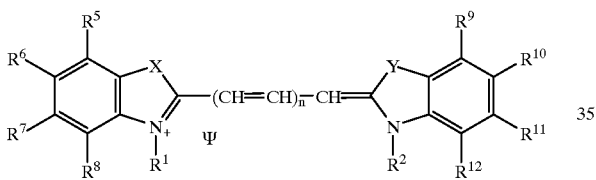

wherein
- $R^1$ and $R^2$ are independently linear or branched hydrocarbons having 7–30 carbons, where each hydrocarbon group optionally incorporates a 5- or 6-membered unsaturated hydrocarbon ring, and each hydrocarbon is independently and optionally substituted one or more times by F, Cl, or alkoxy having 1–6 carbons;
- X and Y are independently O, S or $CR^3R^4$, where $R^3$ and $R^4$, which may be the same or different, are independently alkyl groups having 1–6 carbons, or $R^3$ and $R^4$ taken in combination complete a five or six membered saturated ring;
- n=0–3, yielding a methine bridge that is unsubstituted or is optionally substituted by F, Cl or alkyl having 1–6 carbons; or any double bond in the methine bridge is optionally incorporated into a 5- or 6- membered hydrocarbons ring that is unsubstituted or is optionally substituted one or more times by alkyl having 1–6 carbons;
- $R^5$, $R^6$, $R^7$ $R^8$, $R^9$, $R^{10}$, $R^{11}$ and $R^{12}$ are independently hydrogen, F, Cl, Br, I, CN, sulfo, phenyl, sulfophenyl, polysulfophenyl, carboxy, amino, ammonium, methylbenzamido, or an alkyl group having 1–22 carbons that is optionally and independently substituted by one or more of F, Cl, or $—OR^{13}$ where $R^{13}$ is H or an alkyl group having 1–6 carbons; or any two adjacent substituents of $R^5$, $R^6$, $R^7$, $R^8$, $R^9$, $R^{10}$, $R^{11}$ and $R^{12}$, when taken in combination, form a single fused benzo substituent; or any of $R^5$, $R^6$, $R^7$, $R^8$, $R^9$, $R^{10}$, $R^{11}$ and $R^{12}$ is an —L—A;

wherein
- L is a linking moiety that is a single covalent bond, or is a covalent linkage having 1–20 nonhydrogen atoms selected from the group consisting of C, N, O and S; such that the linkage contains any combination of bonds selected from the group consisting of ether, thioether, amine, ester, carboxamide, sulfonamide and hydrazide bonds; single, double, triple and aromatic carbon-carbon bonds; aromatic and heteroaromatic bonds; and
- A is a reactive group;

Ψ is a biologically compatible counterion, if necessary;

provided that at least one of $R^5$, $R^6$, $R^7$ $R^8$, $R^9$, $R^{10}$, $R^{11}$ or $R^{12}$ is a phenyl, sulfo, sulfophenyl, or polysulfophenyl.

9. A compound, as claimed in claim 8, wherein no more than one of $R^5$, $R^6$, $R^7$ and $R^8$ is a phenyl, sulfo, sulfophenyl or polysulfophenyl, and no more than one of $R^9$, $R^{10}$, $R^{11}$ and $R^{12}$ is a phenyl, sulfo, sulfophenyl or polysulfophenyl.

10. A compound, as claimed in claim 8, wherein no more than one of $R^5$, $R^6$, $R^7$ and $R^8$ is a phenyl, sulfo, sulfophenyl or polysulfophenyl, and none of $R^9$, $R^{10}$, $R^{11}$ and $R^{12}$ is a phenyl, sulfo, sulfophenyl or polysulfophenyl.

11. A compound, as claimed in claim 10, wherein n=1 or 2.

12. A compound, as claimed in claim 8, wherein both $R^1$ and $R^2$ are linear, saturated or unsaturated hydrocarbons that have 12–22 carbons.

13. A compound, as claimed in claim 8, having the formula

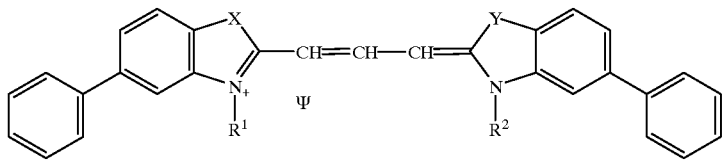

or the formula

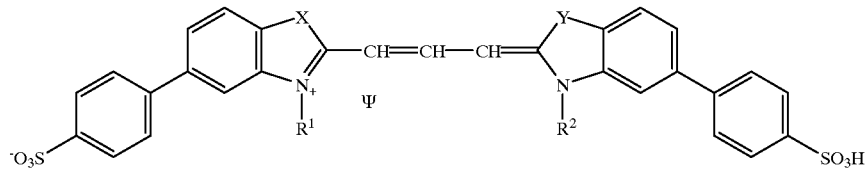

or the formula

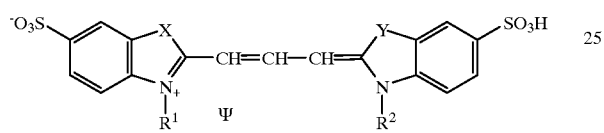

wherein X and Y are each CR³R⁴ or O.

14. A method of staining lipophilic structures in cells, comprising:

combining cells with a cyanine compound of the formula

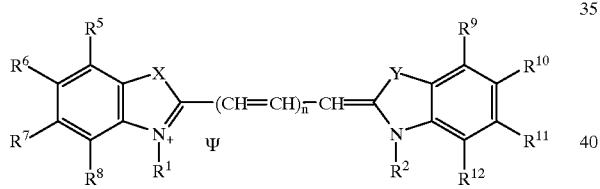

wherein $R^1$ and $R^2$ are independently linear or branched hydrocarbons having 7–30 carbons, where each hydrocarbon group optionally incorporates a 5- or 6-membered unsaturated hydrocarbon ring, and each hydrocarbon is independently and optionally substituted one or more times by F, Cl, or alkoxy having 1–6 carbons;

X and Y are independently O, S or $CR^3R^4$, where $R^3$ and $R^4$, which may be the same or different, are independently alkyl groups having 1–6 carbons, or $R^3$ and $R^4$ taken in combination complete a five or six membered saturated ring;

n=0–3, yielding a methine bridge that is unsubstituted or is optionally substituted by F, Cl or alkyl having 1–6 carbons; or any double bond in the methine bridge is optionally incorporated into a 5- or 6- membered hydrocarbons ring that is unsubstituted or is optionally substituted one or more times by alkyl having 1–6 carbons;

$R^5$, $R^6$, $R^7$ $R^8$, $R^9$, $R^{10}$, $R^{11}$ and $R^{12}$ are independently hydrogen, F, Cl, Br, I, CN, sulfo, phenyl, sulfophenyl, polysulfophenyl, carboxy, amino, ammonium, methylbenzamido, or an alkyl group having 1–22 carbons that is optionally and independently substituted by one or more of F, Cl, or $—OR^{13}$ where $R^{13}$ is H or an alkyl group having 1–6 carbons; or any two adjacent substituents of $R^5$, $R^6$, $R^7$, $R^8$, $R^9$, $R^{10}$, $R^{11}$ and $R^{12}$, when taken in combination, form a single fused benzo substituent; or any of $R^5$, $R^6$, $R^7$, $R^8$, $R^9$, $R^{10}$, $R^{11}$ and $R^{12}$ is a methylbenzamido, chloromethylbenzamido, maleimidyl benzamido, maleimidyl alkylamido, azidobenzamido, azidoperfluorobenzamido, phenyl, sulfo, sulfophenyl, or polysulfophenyl;

Ψ is a biologically compatible counterion, if necessary;

provided that at least one of $R^5$, $R^6$, $R^7$, $R^8$, $R^9$, $R^{10}$, $R^{11}$ or $R^{12}$ is a methylbenzamido, chloromethylbenzamido, maleimidyl benzamido, maleimidyl alkylamido, azidobenzamido, azidoperfluorobenzamido, phenyl, sulfo, sulfophenyl, or polysulfophenyl; and no more than one of $R^5$, $R^6$, $R^7$ and $R^8$, and no more than one of $R^9$, $R^{10}$, $R^{11}$ or $R^{12}$ is a methylbenzamido, chloromethylbenzamido, maleimidyl benzamido, maleimidyl alkylamido, azidobenzamido, or azidoperfluorobenzamido;

where said compound is present in an amount sufficient to selectively accumulate in said lipophilic structures and for a time sufficient for the cyanine compound to selectively accumulate in said lipophilic structures.

15. A method, as claimed in claim 14, wherein the cyanine compound is present as a labeling solution.

16. A method, as claimed in claim 14, wherein said lipophilic structures are biological cells, liposomes or lipoproteins.

17. A method, as claimed in claim 16, wherein said lipophilic structures are biological cells.

18. A method, as claimed in claim 17, further comprising fixing said biological cells.

19. A method, as claimed in claim 17, further comprising fixing and permeabilizing said biological cells.

20. A method, as claimed in claim 14, further comprising observing said stained lipophilic structures using microscopy.

21. A method, as claimed in claim 17, further comprising observing said biological cells using flow cytometry.

22. A method, as claimed in claim 21, further comprising sorting said biological cells.

23. A method, as claimed in claim 14, further comprising adding an additional detection reagent.

24. A method, as claimed in claim 14, wherein said cyanine compound is retained in said cells through cell division or proliferation.

25. A method, as claimed in claim 24, further comprising measuring changes in levels of said cyanine compound in said biological cells through cell division or proliferation.

26. A method, as claimed in claim 14, wherein said cyanine compound is retained in said cells for up to 6 days.

27. A method, as claimed in claim 24, wherein said biological cells are sorted from cells that do not contain said cyanine compound.

28. A method, as claimed in claim 14, wherein said cyanine compound has the formula

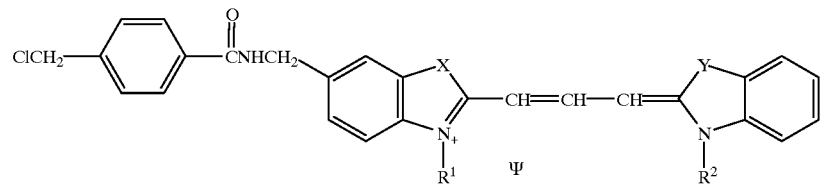

or the formula

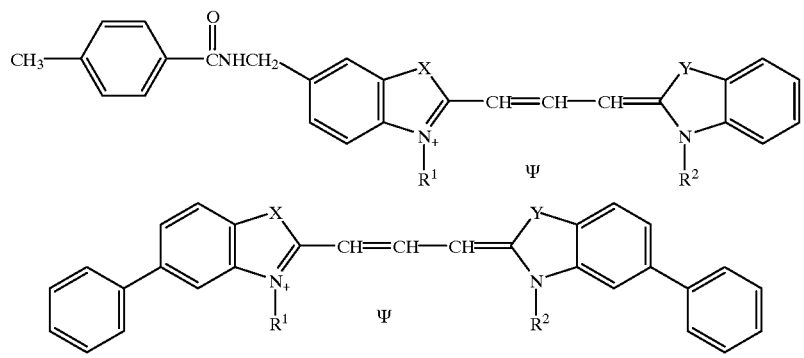

or the formula

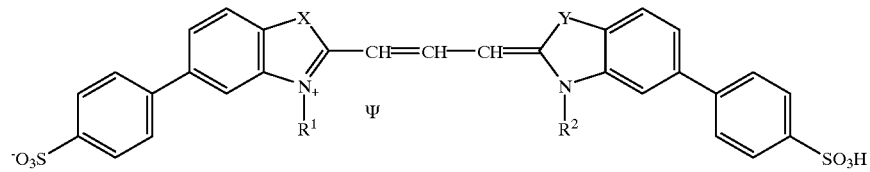

or the formula

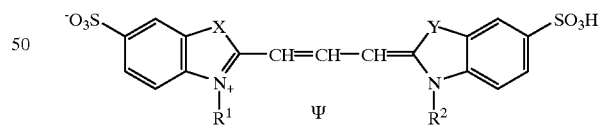

wherein X and Y are each $CR^3R^4$ or O.

* * * * *